United States Patent
Mannino et al.

(10) Patent No.: US 9,566,237 B2
(45) Date of Patent: Feb. 14, 2017

(54) GEODATE DELIVERY VEHICLES

(71) Applicant: Rutgers, the State University of New Jersey, New Brunswick, NJ (US)

(72) Inventors: Raphael J. Mannino, Annandale, NJ (US); Sara L. Krause-Elsmore, Kearny, NJ (US); Susan Gould-Fogerite, Annandale, NJ (US); David Delmarre, Jersey City, NJ (US); Ruying Lu, New Providence, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 13/854,487

(22) Filed: Apr. 1, 2013

(65) Prior Publication Data
US 2013/0224284 A1     Aug. 29, 2013

Related U.S. Application Data

(63) Continuation of application No. 12/657,668, filed on Jan. 25, 2010, now abandoned, which is a continuation
(Continued)

(51) Int. Cl.
*A61K 9/127* (2006.01)
*A61K 9/107* (2006.01)
*A61K 9/16* (2006.01)

(52) U.S. Cl.
CPC ............... *A61K 9/127* (2013.01); *A23L 33/10* (2016.08); *A23L 33/175* (2016.08); *A23P 10/35* (2016.08);
(Continued)

(58) Field of Classification Search
CPC ............................. A61K 9/1274; A61K 9/127
(Continued)

(56) References Cited

U.S. PATENT DOCUMENTS

| 4,078,052 A | 3/1978 | Papahadjopoulos |
| 4,684,633 A | 8/1987 | Imagawa et al. |

(Continued)

FOREIGN PATENT DOCUMENTS

| EP | 1258249 A1 | 11/2012 |
| JP | 2002519316 A | 7/2002 |

(Continued)

OTHER PUBLICATIONS

Asai Y, Watanabe S.Interaction of soybean oil with phosphatidylcholine and their formation of small dispersed particles. Drug Dev Ind Pharm. May 1999;25(5):643-50.
(Continued)

*Primary Examiner* — Gollamudi Kishore
(74) *Attorney, Agent, or Firm* — MH2 Technology Law Group, LLP

(57) ABSTRACT

The present invention provides geodate delivery vehicles and methods of manufacture and administration. A vehicle including a lipid monolayer disposed about a hydrophobic domain is disclosed, that can be part of an emulsion or other mixture, or further disposed in a lipid strata. A vehicle including a lipid strata disposed about a hydrophobic domain is also disclosed. The vehicle can be incorporated into a variety of medicinal, food preparations, and personal care products to deliver or stabilize a cargo moiety. Packaged delivery vehicles for later addition of cargo moieties are also contemplated.

41 Claims, 19 Drawing Sheets

Related U.S. Application Data of application No. 10/701,364, filed on Nov. 3, 2003, now abandoned.

(60) Provisional application No. 60/422,989, filed on Nov. 1, 2002, provisional application No. 60/440,284, filed on Jan. 14, 2003, provisional application No. 60/507,361, filed on Sep. 29, 2003.

(52) U.S. Cl.
CPC ............. *A61K 9/107* (2013.01); *A61K 9/1274* (2013.01); *A61K 9/1617* (2013.01)

(58) Field of Classification Search
USPC ........................................................ 424/450
See application file for complete search history.

(56) References Cited

U.S. PATENT DOCUMENTS

| | | |
|---|---|---|
| 5,061,484 A | 10/1991 | Heldebrant |
| 5,478,860 A | 12/1995 | Wheeler et al. |
| 5,635,357 A | 6/1997 | Malick et al. |
| 5,637,318 A | 6/1997 | Gross et al. |
| 5,840,707 A | 11/1998 | Mannino et al. |
| 2002/0041861 A1 | 4/2002 | Brey et al. |
| 2003/0152635 A1 | 8/2003 | Heurtault et al. |
| 2004/0213837 A1 | 10/2004 | Mantripragada et al. |

FOREIGN PATENT DOCUMENTS

| | | |
|---|---|---|
| JP | 2003001097 A | 1/2003 |
| JP | 2003525257 A | 8/2003 |
| WO | 91/07171 A1 | 5/1991 |
| WO | 93/15720 A1 | 8/1993 |
| WO | 95/09648 A1 | 4/1995 |
| WO | 9701360 | 1/1997 |
| WO | WO-97/30725 A1 | 8/1997 |
| WO | 98/00110 A1 | 1/1998 |
| WO | WO-98/42383 A1 | 10/1998 |
| WO | 99/56727 A2 | 11/1999 |
| WO | 0000177 | 1/2000 |
| WO | 0074653 | 12/2000 |
| WO | 0164328 | 9/2001 |
| WO | 03103822 | 12/2003 |

OTHER PUBLICATIONS

Asai Y, Watanabe S. Formation and stability of the dispersed particles composed of retinyl palmitate and phosphatidylcholine. Pharm Dev Technol. 2000;5(1):39-45.

Asai Y, Watanabe S. Interaction of retinol with dipalmitoylphosphatidylcholine and their formation of small dispersed particles. Chem Phys Lipids. May 1999;99(1):87-93.

Asai Y. Formation of the dispersed particles composed of retinol and phosphatidylchiline. Int J Pharm. Mar. 6, 2003;253 (1-2):89-95.

Asai Y, Watanabe S. Formation and structure of stably dispersed particles composed of retinal with dipalmitoylphosphatidylcholine: coexistence of emulsion particles with bilayer vesicles. Eur J Pharm Biopharm. Jul. 1999;48(1):77-83.

Davis SS, Washington C, West P, Ilium L, Liversidge G, Sternson L, Kirsh R. Lipid emulsions as drug delivery systems. Ann N Y Acad Sci. 1987;507:75-88.

Davis SS, Hansrani P.The stabilization of intravenous fat emulsions using phospholipids. The effect of minor components [proceedings] J Pharm Pharmacol. Dec. 1979;31 Suppl:2P.

Hou RC, Lin MY, Wang MM, Tzen JT. Increase of viability of entrapped cells of *Lactobacillus delbrueckii* ssp. bulgaricus in artificial sesame oil emulsions. J Dairy Sci. Feb. 2003;86(2):424-8.

Lee HS, Coates GA. Characterization of color fade during frozen storage of red grapefruit juice concentrates. J Agric Food Chem. Jul. 3, 2002;50(14):3988-91.

Li M, Murphy DJ, Lee KH, Wilson R, Smith LJ, Clark DC, Sung JY. Purification and structural characterization of the central hydrophobic domain of oleosin. J Biol Chem. Oct. 4, 2002;277(40):37888-95. Epub Jul. 17, 2002.

Ramkumar C, Singh H, Munro PA, Singh AM. Influence of calcium, magnesium, or potassium ions on the formation and stability of emulsions prepared using highly hydrolyzed whey proteins. J Agric Food Chem. May 2000;48 (5):1598-604.

Rubino JT. The influence of charged lipids on the flocculation and coalescence of oil-in-water emulsions. I: Kinetic assessment of emulsion stability. J Parenter Sci Technol. Jul.-Aug. 1990;44(4):210-5.

Rubino JT. The influence of charged lipids on the flocculation and coalescence of oil-in-water emulsions. II: Electrophoretic properties and monolayer film studies. J Parenter Sci Technol. Sep.-Oct. 1990;44(5):247-52.

Silvander M, Hellstrom A, Warnheim T, Claesson P. Rheological properties of phospholipid-stabilized parenteral oil-in-water emulsions—effects of electrolyte concentration and presence of heparin. Int J Pharm. Feb. 18, 2003;252(1-2):123-32.

Wassail SR, McCabe RC, Ehringer WD, Stillwell W. Effects of dietary fish oil on plasma high density lipoprotein. Electron spin resonance and fluorescence polarization studies of lipid ordering and dynamics. J Biol Chem. Apr. 25, 1992,267(12):8168-74.

Mitsuo Matsumoto, "A Yakuzaigaku Manual (A Manual for Pharmaceuticals)", Ist edition, Nanzando Co., Ltd. (1989), in Japanese, p. 121.

Zarif et al., Antimicrobial Agents and Chemotherapy, Jun. 2000, p. 1463-1469 (vol. 44, No. 6).

Thomas Brandenburg, Opposition in EP 1562557 and English language translation thereof, dated Jan. 7, 2014, pp. 1-31.

Chantal Ullrich (Formalities Officer), Communication of Notice of Opposition in EP 1562557, dated Jan. 22, 2014, p. 1.

C. Ullrich (Formalities Officer), Communication of Notices of Opposition in EP 1562557, dated Feb. 14, 2014, p. 1.

Thorsten Bausch, Observations on the Opposition to EP 1562557, dated Oct. 24, 2014, pp. 1-43.

Summons to Attend Oral Proceedings Pursuant to Rule 115(1) EPC in EP 1562557, dated Feb. 24, 2015, pp. 1-13.

Thomas Brandenburg, Reply to Patent Proprietor's Brief in EP 1562557 and English language translation thereof, dated Feb. 27, 2015, pp. 1-17.

Translation of excerpts from "Surfactants of the Slide Presentation Series", produced by the Fonds der Chemischen Industrie, 1982, pp. 1-18.

Hans Peter Latscha et al., "Organische Chemie, Chemie—Basiswissen II", Chapter 43, Berlin, Springer-Verlag and English language translation excerpts, Jan. 1993, pp. 1-6.

V Prasad et al., "Confocal microscopy of colloids", Journal of Physics: Condensed Matter, vol. 19, 2007, pp. 1-26.

D. Papahadjopoulos et al., "Cochleate Lipid Cylinders: Formation by Fusion of Unilamellar Lipid Vesicles", Biochimica et Biophysica Acta 394, Apr. 1975, pp. 483-491.

Jing Li et al., "A review on phospholipids and their main applications in drug delivery systems", Asian Journal of Pharmaceutical Science, vol. 10, Issue 2, Apr. 2015, pp. 81-98.

V. Ravi Sankar et al., "Nanocochleate—A New Approach in Lipid Drug Delivery", International Journal of Pharmacy and Pharmaceutical Sciences, vol. 2, Issue 4, May 2010, pp. 220-223.

Salome Amarachi Chime et al., "Lipid-based drug delivery systems (LDDS): Recent advances and applications of lipids in drug delivery", African Journal of Pharmacy and Pharmacology, vol. 7, Dec. 29, 2013, pp. 3034-3059.

Tarinee Pongsaanutin et al., "Fabrication and Characterisation of Calcium Phosphate—Liposome Composites as an Implant Coating", Materials Research Society Symp. Proc. vol. 662, 2001, pp. 1-5.

Opposition by Fresenius Kabi in EP 1562557 and English language translation thereof, dated Sep. 11, 2015, pp. 1-6 (including translation).

Opposition by Fresenius Kabi in EP 1562557 and English language translation thereof, dated Nov. 9, 2015, pp. 1-6 (including translation).

GEODATE DELIVERY VEHICLES

RELATED APPLICATIONS

This application is a continuation of U.S. Utility application Ser. No. 12/657,668, filed Jan. 25, 2010, which, in turn, is a continuation of U.S. Utility application Ser. No. 10/701,364, filed Nov. 3, 2003 and now abandoned, which claims the benefit of U.S. Provisional Application Nos. 60/422,989, filed Nov. 1, 2002; 60/440,284, filed Jan. 14, 2003; and 60/507,361, filed Sep. 29, 2003, the entire contents of each of the aforementioned applications are hereby incorporated herein by reference.

BACKGROUND

Liposomes are widely described in the literature, and their structure is well known. Typically, they have an onion-like multilamellar structure comprising a plurality of lipid bilayers spaced one from another by aqueous material. Another type of liposome is a unilamellar liposome, sometimes referred to as a vesicle, which is a single lipid bilayer disposed about an aqueous material.

The use of liposomes as carriers or vehicles for drugs is known, and can be achieved by a variety of methods. One method involves casting a film of lipid by evaporation from a solution in an organic solvent, for example chloroform, and then dispersing the film in a suitable aqueous medium. In the case of lipid-soluble biologically active compounds, that is, those which associate with the lipid layers rather than the aqueous phase of the liposomes, the compound can be cast as a film together with a phospholipid, using a common organic solvent. A disadvantage of this method is that the amount of active compound that can be incorporated into the lipid bilayer is limited. Additionally, the casting method can not be scaled up to accommodate large batches. In the case of water-soluble biologically active compounds the compound is typically associated with liposomes by dispersing a cast lipid film with an aqueous solution in which the compound is solubilized. Disadvantages of this method include the difficulty of incorporating sufficient quantities of the active compound in the vesicles, and instability and shelf life of the dispersion. Another disadvantage of this method is the presence of trace amounts of solvent used in the creation of the vesicles.

The loss of the biologically active compound from liposomes into external aqueous medium is another factor which restricts the potential of these preparations as practical dosage forms. This is particularly the case for not only low molecular weight, water-soluble compounds, but also for lipid-soluble compounds, both of which can partition into the external aqueous medium until equilibrium is reached. If the concentration of compound is small, and/or the volume of the external aqueous medium is large, this loss can represent a significant proportion of the total amount of the biologically active compound in the liposomes.

SUMMARY OF THE INVENTION

The present invention provides new delivery vehicles for cargo moieties that are stable and capable of delivering desired amounts of active agent. The present invention is based, at least in part, on the discovery that geodate delivery vehicles can be formed that include a lipid monolayer formed about a hydrophobic domain. The hydrophobic domain can include one or more cargo moieties at concentrations previously unattainable by incorporating hydrophobic agents into liposomal bilayers.

The present invention also is based, in part, on the discovery that the delivery vehicles can be locked within a crystal strata of alternating cation and lipid sheet layers. The encrustation can optionally be removed prior to administration or administered in an encrusted state. The present invention further provides novel methods of manufacture of the delivery vehicles, including vehicles in emulsion and crystallized form. Encrusted or crystallized vehicles can be conveniently and stably added to further preparations, such as food, and retain their integrity until ingested, retaining the cargo moiety in a stable, non-degraded state. Methods of administration and incorporation are also disclosed.

Thus, in one embodiment, the present invention provides a geodate delivery vehicle for a cargo moiety which includes a lipid monolayer disposed about a hydrophobic domain and a lipid strata disposed about the lipid monolayer. In another embodiment, the invention provides a geodate delivery vehicle for a cargo moiety which includes a lipid monolayer disposed about a hydrophobic domain, wherein the lipid monolayer includes a phospholipid.

In some embodiments, the geodate delivery vehicle of the present invention is suspended in an aqueous environment. Additionally or alternatively, the geodate delivery vehicle is suspended in an emulsion. In another embodiment, the geodate delivery vehicle is in powder form.

In some embodiments, the geodate delivery vehicle of includes a cargo moiety associated with the geodate delivery vehicle. In one embodiment, the cargo moiety is associated with the hydrophobic domain. In another embodiment, the hydrophobic domain is a cargo moiety. In a third embodiment, the cargo moiety is associated with the lipid monolayer or the lipid strata. In a fourth embodiment, the hydrophobic domain includes a cargo moiety associated with an oil or fat. In preferred embodiments, the cargo moiety is a vitamin, a mineral, a nutrient, a micronutrient, an amino acid, a toxin, a microbicide, a microbistat, a co-factor, an enzyme, a polypeptide, a polypeptide aggregate, a polynucleotide, a lipid, a carbohydrate, a nucleotide, a starch, a pigment, a fatty acid, a monounsaturated fatty acid, a polyunsaturated fatty acid, a flavor substance, a flavored essential oil or extract, a hormone, a cytokine, a virus, an organelle, a steroid or other multi-ring structure, a saccharide, a metal, a metabolic poison, an antigen, an imaging agent, a porphyrin, a tetrapyrrolic pigment, or a drug.

In one aspect of the invention, the lipid includes a negatively charged phospholipid. Preferably, the lipid includes at least about 50% negatively charged lipid, and more preferably, the lipid includes at least about 75% negatively charged lipid.

In some embodiments, the geodate delivery vehicle includes an aggregation inhibitor. Preferably, the aggregation inhibitor is casein or methylcellulose.

In one aspect, the present invention provides a geodate delivery vehicle packaged with instructions for incorporating a cargo moiety. In another aspect, the invention provides a geodate delivery vehicle packaged with instructions for adding the vehicle to a food, beverage or personal care product.

In another aspect, the present invention provides a food item containing a geodate delivery vehicle. The food item can be an animal food item, a human food item, a nutrient bar, a snack food, a beverage, a domesticated animal food, a fish food, a poultry feed, a pet food, a dog food or a cat food.

In yet another aspect, the present invention provides a personal care product containing a geodate delivery vehicle. The personal care product can be a hair care product or a skin care product.

In other embodiments, the present invention provides a pharmaceutical composition including a geodate delivery vehicle and a pharmaceutically acceptable carrier.

In another aspect, the present invention provides a method of treating a subject that can benefit from the administration of a cargo moiety, comprising the step of administering a geodate delivery vehicle comprising a cargo moiety to a subject. The route of administration can be mucosal, systemic, oral, intranasal, intraocular, intrarectal, intravaginal, intrapulmonary, intravenous, intramuscular, subcutaneous, transdermal or intradermal. In some embodiments, the cargo moiety is administered to treat inflammation, pain, infection, fungal infection, bacterial infection, viral infection, parasitic disorders, an immune disorder, genetic disorders, degenerative disorders, cancer, diabetes, insomnia, proliferative disorders, obesity, depression, hair loss, impotence, hypertension, hypotension, dementia, senile dementia, or malnutrition. In other embodiments, the subject can benefit from administration of a nutrient and the cargo moiety is a nutrient.

In another embodiment, the present invention provides a method of manufacturing a geodate delivery vehicle for a cargo moiety by mixing a lipid, an aqueous solution and a hydrophobic material, such that a lipid monolayer is disposed about a hydrophobic domain. In another embodiment, the geodate delivery vehicle can additionally include a cargo moiety. In yet another embodiment, a lipid strata can be formed about the lipid monolayer by adding a multivalent cation. Preferably, the multivalent cation includes calcium.

In some embodiments, the geodate delivery vehicle is dried to form a powder. In other embodiments, the geodate delivery vehicle is associated with a pharmaceutically acceptable carrier. In still other embodiments, the geodate delivery vehicle is added to a food item or a personal care product.

The present invention also provides a method of forming a geodate delivery vehicle for a cargo moiety by mixing a lipid which includes a phospholipid with a hydrophobic material such that a geodate delivery vehicle is formed.

BRIEF DESCRIPTION OF THE DRAWINGS

FIGS. 13A and 13B depict geodes in suspension and FIGS. 13C and 13D depict the same formulations subsequent to the addition of EDTA.

FIGS. 14A and 14D are images of geodes extracted by spray drying, and FIGS. 14B and 14C are images of geodes extracted by fluid bed drying.

DETAILED DESCRIPTION OF THE INVENTION

Figure 1:
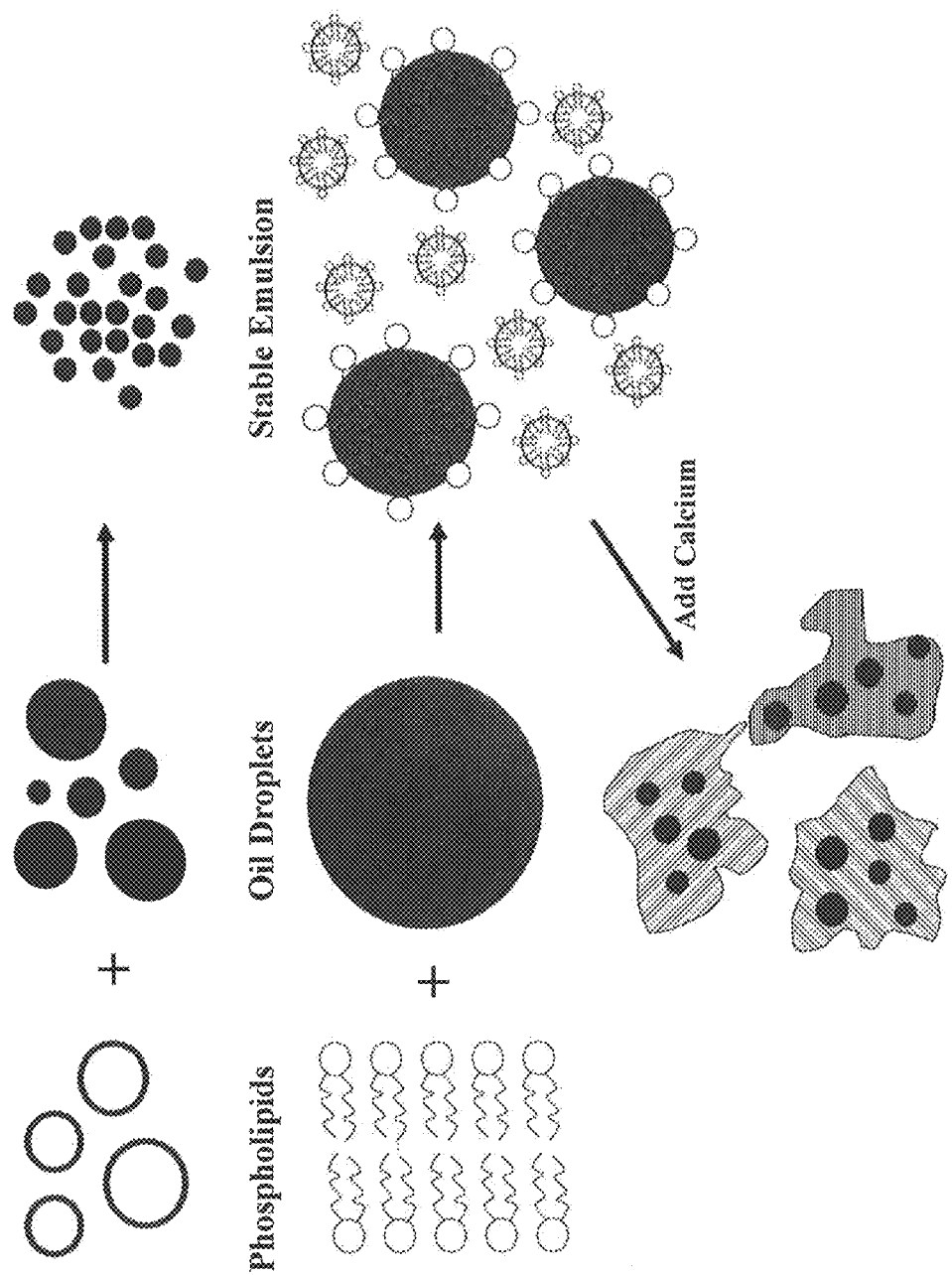
FIG. 1 illustrates an exemplary method of manufacturing a geodate delivery vehicle in accordance with the present invention.
Figure 2:
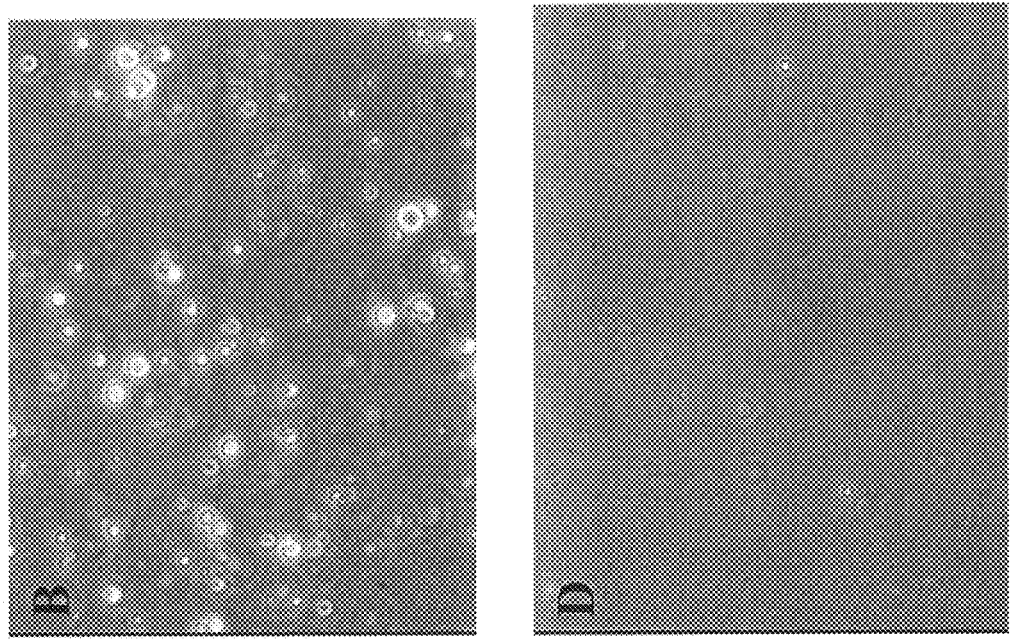
FIGS. 2A-D are four images of dioleoyl phosphatidylserine (DOPS) and olive oil interacting an aqueous buffer.
Figure 2:
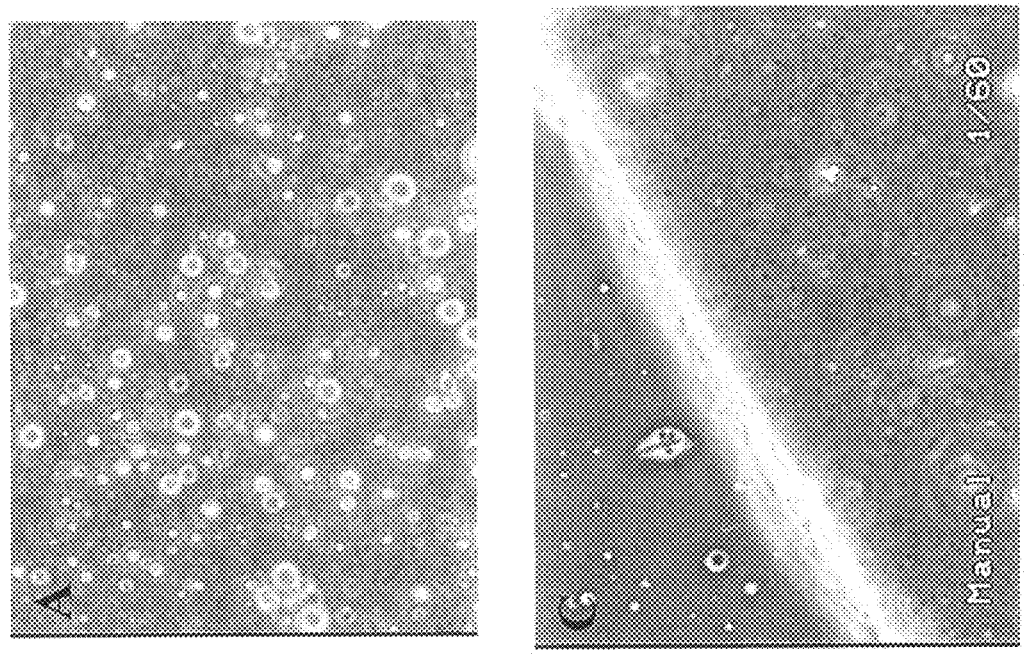

The invention is based, in part, on the discovery that a lipid monolayer will form about a hydrophobic domain, and that this structure can be employed to deliver a variety of cargo moieties.

One advantage of the present invention is that cargo moieties can be incorporated into the geodate delivery vehicle at high concentrations. Another advantage of the present invention is the ability to incorporate multiple cargo moieties into one geodate delivery vehicle. Incorporation into a geodate delivery vehicle is also advantageous because it provides the cargo moiety with protection from both the environment, e.g., water and oxygen, and also the stomach. Additionally, the geodate delivery vehicle protects stomach from the cargo moiety. The present invention is advantageous because the formulation of geodate delivery vehicles involves no solvent. The present invention is also advantageous because the resultant geodate delivery vehicles are highly stable, e.g., they can withstand extreme temperature and pressure. Another advantage of the present invention is the ability of the geodate delivery vehicle to mask the taste and/or odor of cargo moieties.

In order to more clearly and concisely describe the subject matter of the claims, the following definitions are intended to provide guidance as to the meaning of specific terms used in the following written description, examples and appended claims.

The term "geodate delivery vehicle" refers to a delivery vehicle for a cargo moiety. Geodate delivery vehicles generally include a lipid monolayer disposed about a hydrophobic domain. A "hydrophobic domain" is a composition that is sufficiently hydrophobic in nature to allow formation of a lipid monolayer about its periphery. A hydrophobic domain can itself be one or more cargo moieties, or it can include a hydrophobic composition, such as oil or fat, associated with the cargo moiety, which can be, e.g., a hydrophobic or amphiphilic agent.

The term "lipid monolayer" generally refers to a lipid-containing layer one molecule thick (as contrasted with lipid bilayers that are two molecules thick). A lipid monolayer can contain further elements, such as cholesterol, steroids, or proteins. In contrast, "liposomes" refer to vesicles defined by lipid bilayers (two molecules thick) in a unilamellar or multilamellar structure.

In one aspect of the invention, the lipid monolayer includes and/or is composed primarily of negatively charged lipids. When a lipid strata is formed, the multivalent cation forms a cationic bridge between the negatively-charged lipid in the monolayer and the negatively charged lipid in the liposomes. In another embodiment, the lipid monolayer is composed primarily of positively charged lipids. In this case, the head groups interact with negatively charged lipid in the strata. In yet another embodiment, the lipid monolayer is composed primarily of neutral lipids. The coated hydrophobic domain, in this embodiment is trapped within the lipid strata, but does not ionically interact with the strata.

The term "lipid strata" refers to a structure of alternating cationic and lipid sheet-like layers. A lipid strata can be formed by introducing a cation to an emulsion containing liposomes. The lipid strata not only locks the hydrophobic domain within the geodate lipid monolayer, but can itself be associated with a cargo moiety (e.g., a hydrophilic agent disposed within the lipid strata). In one embodiment, the lipid strata entraps a hydrophobic domain. In another, the lipid strata entraps a hydrophobic domain disposed within a lipid monolayer.

The term "cargo moiety" refers to any compound having a property of biological interest. The agent may be, e.g., organic or inorganic, a monomer or a polymer, endogenous to a host organism or not, naturally occurring or synthesized in vitro and the like. Thus, examples include, vitamins, minerals, nutrients, micronutrients, amino acids, toxins, microbicides, microbistats, co-factors, enzymes, polypeptides, polypeptide aggregates, polynucleotides, lipids, carbohydrates, nucleotides, starches, pigments, fatty acids, monounsaturated fatty acids, polyunsaturated fatty acids, flavorings, essential oils or extracts, hormones, cytokines, viruses, organelles, steroids and other multi-ring structures, saccharides, metals, medicaments, proteins, marker compounds, imaging agents, antigens, porphyrins, tetrapyrrolic pigments, metabolic poisons, drugs and the like The methods of this invention are particularly useful in the case of hydrophobic cargo moieties and agents that can be associated with and/or can be incorporated into a hydrophobic phase, e.g., by binding to or admixing with a hydrophobic vehicle. Cargo moieties can also be incorporated in a lipid strata of the present invention. Thus, combination therapies can be employed by delivering one or more active agents (e.g., hydrophobic and amphiphilic agents) associated with the hydrophobic domain, and one or more active agents (e.g., hydrophilic agents) associated with the lipid strata.

In one embodiment, the invention provides a geodate delivery vehicle for a cargo moiety, which includes a lipid monolayer disposed a hydrophobic domain, and a lipid strata disposed about the lipid monolayer. In another embodiment, the invention provides a geodate delivery vehicle for a cargo moiety including a lipid monolayer disposed a hydrophobic domain, and wherein the lipid monolayer includes at least one phospholipid.

In one embodiment, the geodate delivery vehicle can be suspended in an aqueous environment, e.g., an emulsion. In alternative embodiments, the geodate delivery vehicle is in powder form.

The hydrophobic domain is a hydrophobic composition that can be a carrier for one or more cargo moieties, or the cargo moiety or agents itself. That is, the hydrophobic domain can be a hydrophobic carrier (e.g., olive oil or soy oil) associated with a cargo moiety (e.g., an antifungal agent such as amphotericin, a marker compound such as rhodamine, and/or nutrients such as beta carotene and alpha tocopherol). Alternatively, the hydrophobic domain can be the cargo moiety itself, e.g., a nutrient such as omega 3 fatty acid or a hydrophobic drug. Alternatively the hydrophobic domain can be one or more cargo moieties that act as a carrier for further cargo moieties.

In one embodiment, the hydrophobic domain is present in a range of between about 1% and 99%, preferably between about 1% and about 75%, more preferably between about 10% and about 30% by weight of the final composition of the geode.

The terms "encrusted," "crystallized," and "crystalline" generally refer to a solid or semi-solid lipid strata formed about one or more hydrophobic domains.

As used herein, the term "food" refers to any object or objects suitable for consumption by a human or non-human animal.

The term "delivery," as used herein, refers to any means of bringing or transporting a cargo moiety to a host, a food item, a formulation, a pharmaceutical composition, or any other system, wherein the cargo moiety maintains at least a portion of the activity it had when first formulated in the geodate structure. Thus, e.g., in a beta-carotene geode, the beta-carotene retains some activity within the geode until it is used.

The delivery vehicles of the present invention are directed to hydrophobic domains encapsulated or entrapped in a stable vehicle. In one aspect, the invention features a lipid monolayer disposed about a hydrophobic domain, which can be part of a stable emulsion and/or entrapped in lipid strata. In another aspect the geodate delivery vehicle features a lipid strata disposed about a hydrophobic domain, and a lipid monolayer is optional.

The hydrophobic domain can itself be one or more cargo moieties, or it can include a hydrophobic composition (e.g., oil or fat) associated with the cargo moiety, which can be, e.g., a hydrophobic or amphiphilic agent. If the agent is amphiphilic, it can associate with both the hydrophobic domain and the lipid. Further cargo moieties can also be delivered by associating them with a lipid strata, thus combination therapies can be effected. The cargo moiety can be associated with the hydrophobic domain, the lipid monolayer and/or the lipid strata.

The cargo moiety can be a diagnostic agent, such as an imaging agent. Imaging agents include nuclear agents and porphyrins. Porphyrins include tetrapyrrolic agents or pigments. One such tetrapyrrolic agent is Zinc Tetra-Phenyl Porphyrin (ZnTPP), which is a hydrophobic, fluorescent molecule that has high absorption in the visible spectrum (dark purple).

The cargo moiety may be a polynucleotide that is expressed to yield a biologically active polypeptide or polynucleotide. Thus, the polypeptide may serve as an immunogen or, e.g., have enzymatic activity. The polynucleotide may have catalytic activity, for example, be a ribosome, or may serve as an inhibitor of transcription or translation, e.g., a small interfering RNA (siRNA) or an antisense molecule. The polynucleotide can be an antisense molecule including modified antisense molecule, such as an morpholino antisense molecule. The polynucleotide can be modified, e.g., it can be synthesized to have a morpholino backbone. If expressed, the polynucleotide preferably includes the necessary regulatory elements, such as a promoter, as known in the art. A specific example of a polypeptide is insulin. The cargo moiety can be an organic molecule that is hydrophobic in aqueous media. The cargo moiety can be a water-soluble polyvalent cationic molecule.

The cargo moiety can be a drug, such as, a protein, a small peptide, a bioactive polynucleotide, an antibiotic, an antiviral, an anesthetic, an anti-infectious, an antifungal, an anticancer, an immunosuppressant, a steroidal anti-inflammatory, a non-steroidal anti-inflammatory, an antioxidant, an antidepressant which can be synthetic or naturally derived, a substance which supports or enhances mental function or inhibits mental deterioration, an anticonvulsant, an HIV protease inhibitor, a non-nucleophilic reverse transcriptase inhibitor, a cytokine, a tranquilizer or a vasodilatory agent. The drug can also be any over the counter (non-prescription) medication. Examples include Amphotericin B, acyclovir, adriamycin, carbamazepine, ivermectin, melphalen, nifedipine, indomethacin, curcumin, aspirin, ibuprofen, naproxen, acetaminophen, rofecoxib, diclofenac, ketoprofin, meloxicam, nabumetone, estrogens, testosterones, steroids, phenyloin, ergotamines, cannabinoids, rapamycin, propanadid, propofol, alphadione, echinomycin, miconazole nitrate, teniposide, hexamethylmelamine, taxol, taxotere, 18-hydroxydeoxycorticosterone, prednisolone, dexamethazone, cortisone, hydrocortisone, piroxicam, diazepam, verapamil, vancomycin, tobramycin, nystatin, rifampin, geldanamycin, tyrphostin, glucan synthesis inhibitors, vitamin A acid, mesalamine, risedronate, nitrofurantoin, dantrolene, etidronate, caspofungin, nicotine, amitriptyline, clomipramine, citalopram, dothepin, doxepin, fluoxetine, imipramine, lofepramine, mirtazapine, nortriptyline, paroxetine, reboxitine, sertraline, trazodone, venlafaxine, dopamine, St. John's wort, phosphatidylserine, phosphatidic acid, amastatin, antipain, bestatin, benzamidine, chymostatin, 3,4-dichloroisocoumarin, elastatinal, leupeptin, pepstatin, 1,10-phenanthroline, phosphoramidon, ethosuximide, ethotoin, felbamate, fosphenyloin, lamotrigine, levitiracetam, mephenyloin, methsuximide, oxcarbazepine, phenobarbital, phensuximide, primidone, topirimate, trimethadione, zonisamide, saquinavir, ritonavir, indinavir, nelfinavir, or amprenavir.

The drug can be a polypeptide such as cyclosporin, angiotensin I, II and III, enkephalins and their analogs, ACTH, anti-inflammatory peptides I, II, III, bradykinin, calcitonin, b-endorphin, dinorphin, leucokinin, leutinizing hormone releasing hormone (LHRH), insulin, neurokinins, somatostatin, substance P, thyroid releasing hormone (TRH) and vasopressin.

The drug can be an antigen, but is not limited to a protein antigen. The antigen can also be a carbohydrate or DNA. Examples of antigenic proteins include membrane proteins, carbohydrates, envelope glycoproteins from viruses, animal cell proteins, plant cell proteins, bacterial proteins, and parasitic proteins.

The antigen can be extracted from the source particle, cell, tissue, or organism by known methods. Biological activity of the antigen need not be maintained. However, in some instances (e.g., where a protein has membrane fusion or ligand binding activity or a complex conformation which is recognized by the immune system), it is desirable to maintain the biological activity. In these instances, an extraction buffer containing a detergent which does not destroy the biological activity of the membrane protein is employed. Suitable detergents include ionic detergents such as cholate salts, deoxycholate salts and the like or heterogeneous polyoxyethylene detergents such as Tween, BRIG or Triton.

The cargo moiety can be a nutrient including, but not limited to, lycopene, micronutrients such as phytochemicals or zoochemicals, vitamins, minerals, fatty acids, amino acids, fish oils, fish oil extracts, and saccharides, vitamins, herbal products, essential oils or minerals. Specific examples include Vitamins A, B, B1, B2, B3, B12, B6, B-complex, C, D, E, and K, vitamin precursors, caroteniods, and beta-carotene, resveratrol, biotin, choline, inositol, ginko, lutein, zeaxanthine, quercetin, silibinin, perillyl alcohol, genistein, sulfurophane, omega-3 and omega-6 fatty acids, herbs, spices, and iron. Minerals include, but are not limited to boron, chromium, colloidal minerals, colloidal silver, copper, manganese, potassium, selenium, vanadium, vanadyl sulfate, calcium, magnesium, barium, iron and zinc.

As used herein, "micronutrient" is a nutrient that the body must obtain from outside sources. Generally micronutrients are essential to the body in small amounts.

The cargo moiety can be a saccharide or sweetener, e.g., saccharine, isomalt, maltodextrine, aspartame, glucose, maltose, dextrose, fructose and sucrose. Flavor agents include oils, essential oils, or extracts, including but not limited to oils and extracts of cinnamon, vanilla, almond, peppermint, spearmint, chamomile, geranium, ginger, grapefruit, hyssop, jasmine, lavender, lemon, lemongrass, marjoram, lime, nutmeg, orange, rosemary, sage, rose, thyme, anise, basil, black pepper, tea or tea extracts, an herb, a citrus, a spice or a seed.

In one embodiment, the cargo moiety is present in a range of between approximately 1% and 99% of the final composition. In one embodiment, the cargo moiety is present in a range between about 1% and about 30% by weight of the final composition of the geode. In another embodiment, a second cargo moiety is additionally incorporated into the geode structure, in a range of between about 0.1% and about 90% by weight of the final composition of the geode. In one embodiment, the second cargo moiety is present in a range of between about 1% and about 10%, more preferably between about 1% and about 5%.

In one embodiment, the cargo moiety is incorporated into the hydrophobic domain in a range of between about 0.1% and about 99% of the hydrophobic domain. In a preferred embodiment, the range is between about 0.1% and about 50%. More preferably, the ratio is between about 1% and about 25%. In another embodiment, a second cargo moiety is also incorporated into the hydrophobic domain in a range of between about 1% and about 90%. In another embodiment the cargo moiety is the hydrophobic domain.

In one embodiment, the hydrophobic domain is present in a range of between about 1% and about 99% of the total composition. In a preferred embodiment, the hydrophobic domain is present in a range of about 1% and about 50% of the total composition. More preferably, the hydrophobic domain is present in a range of about 5% to about 35%.

Lipids suitable for use in forming the lipid monolayer (and the liposomes discussed below) include, but are not limited to, phospholipids such as soy lecithin, partially refined lecithin, hydrogenated phospholipids, lysophosphate, phopshpatidylcholine, phosphatidylethanolamine, phosphatidylserine (PS), phosphatidylinositol, cardiolipin, sphingolipids, gangliosides, cerebrosides, ceramides, soy phospholipids, other ester analogues of phopshpatidylcholine, synthetic phospholipids, phosphatidylethanolamine derivatives, and phospholipids with partially or fully fluorinated fatty acid chains. Preferably, the lipid is a negatively charged phospholipid such as phosphatidylserine. Preferred phosphatidylserines include soy PS and dioleoyl PS (DOPS). The lipid can also include fluorescent phospholipid.

Further, synthetic phospholipids containing either altered aliphatic portions, such as hydroxyl groups, branched carbon chains, cyclo derivatives, aromatic derivatives, ethers, amides, polyunsaturated derivatives, halogenated derivatives, or altered hydrophilic portions containing carbohydrate, glycol, phosphate, phosphonate, quaternary amine, sulfate, sulfonate, carboxy, amine, sulfhydryl, imidazole groups and combinations of such groups, can be either substituted or intermixed with the phospholipids, and others known to those skilled in the art The lipid employed in the present invention preferably includes one or more negatively charged lipids. As used herein, the term "negatively charged lipid" includes lipids having a head group bearing a formal negative charge in aqueous solution at an acidic or physiological pH, and also includes lipids having a zwitterionic head group.

In one embodiment, the lipid is a mixture of lipids, comprising at least 50% negatively charged lipid. In another embodiment, the lipid includes at least 75% negatively charged lipid. In other embodiments, the lipid includes at least 85%, 90%, 95% or even 99% negatively charged lipid. All ranges and values between 40% and 100% negatively charged lipid are meant to be encompassed herein.

In a preferred embodiment, the lipid monolayer formed about the hydrophobic domain is a predominantly negatively charged lipid monolayer. In a preferred embodiment, lipid strata can be formed by the addition of a cation to the emulsion.

In another embodiment, the lipid monolayer formed about the hydrophobic domain is a predominantly positively charged lipid monolayer. In another embodiment, lipid strata may be formed by the addition of an anion to the emulsion.

If the delivery vehicle is suspended in a stable emulsion, the solution can contain liposomes or other lipid structures to further stabilize the emulsion, e.g., to reduce or eliminate aggregation or coalescence within the emulsion. The solution can also include additional additives to prevent aggregation, to aid in the association of cargo moieties with the hydrophobic domains, and/or to prevent the active agent from migrating out of the delivery vehicles of the present invention. If lipid strata is formed about the hydrophobic domains in an emulsion, the vehicles can be utilized in an emulsion or extracted for utility in a solid or semi-solid form such as a paste or a powder.

The lipid monolayer is advantageous because large and/or charged molecules have difficulty passing through it. Thus cargo moieties are inhibited or prevented from exiting the domain through the monolayer. The lipid strata is advantageous because it typically is impassable by cargo moieties which are immobilized within it or trapped by it in the hydrophobic domain. Another advantage to both the monolayer and the lipid strata is that the cargo moiety is protected from the environment and the environment is protected by the cargo moiety. Both the emulsions and the lipid strata are stable, thus enabling not only convenient storage and delivery of the agents, but a convenient means of incorporating the same into compositions, such as food or pharmaceutical compositions.

A lipid strata includes liposomes and cation, and can be formed from liposomes by exposure to cation. The cation and the liposomes align to form a stacked or rolled structure that captures and retains or encrusts one or more hydrophobic domains. The cation preferably is a multivalent cation.

The cation can be a divalent cation, such as $Ca^{++}$, $Zn^{++}$, $Ba^{++}$, and $Mg^{++}$. The cation can also be a multivalent cargo moiety.

The hydrophobic domains, with or without a lipid monolayer dispersed about said hydrophobic domains, can be released from the lipid strata when desired upon exposure of the crystalline lipid structure to a chelating agent such as EDTA, ascorbic acid and/or citric acid. The chelating agent serves to disrupt the crystalline structure providing a de-encrusted lipid monolayer encapsulating a hydrophobic globule. The chelating agent can be added to a dry powder and stored, so that upon addition of water, the chelating agent acts on the encrustation to release the encapsulated domain.

Cargo moieties can be delivered at different rates, depending, e.g., on whether the vehicle is in a lipid strata and/or an emulsion. The choice of cation, lipid and hydrophobic domain makeup can also affect delivery rates and times. Thus, the rate of release of the cargo moieties contained therewith varies and can even be staggered, e.g., if the lipid strata dissolves first in vivo, delivering a first agent, followed by the delivery of a second agent associated with the hydrophobic domain. Accordingly, by controlling the ingredients and the structure of the vehicles described herein, vehicles which will release the cargo moiety in desired amounts over a protracted period of time are obtainable.

Accordingly, the compositions of the invention may include one or more cargo moieties present in or associated with the hydrophobic domain, the lipid monolayer, the lipid strata, a stable emulsion (e.g., in liposomes or aqueous media), or any combination thereof. In addition, several layers of precipitate can be formed about or encrusted about the geodate delivery vehicles, with one or more cargo moieties associated therewith. Accordingly, the invention may be employed for combination drug therapy and/or consecutive or simultaneous release profiles, e.g., pulsed or extended release. For example, a stomach protecting medication can be formulated in the lipid strata for initial release, and one or more non-steroidal anti-inflammatory drugs can be formulated in the hydrophobic domain for release after the stomach protecting medication is released.

The amount of cargo moiety incorporated into the vehicles of the present invention can vary. Because of the advantageous properties of the vehicles, e.g., the stability of the agent trapped in the vehicle, lesser amounts of the agent can be used to achieve the same end result as compared to using known delivery means, e.g., direct addition of the agent to food.

In one embodiment, the geodate delivery vehicles of the present invention are small, e.g., in the micrometer or nanometer range. Such geodate delivery vehicles are particularly advantageous, e.g., because the small size increases the oral availability. In addition, small sizes are preferred and sometimes necessary for intravenous administration. The geodate delivery vehicles of the invention can be micronized or disaggregated by introducing an aggregation inhibitor (e.g., casein). Preferably, however, the geodate delivery vehicles are formed in the desired size range and/or the suspension can be micronized prior to addition of cation. In such embodiments, an aggregation inhibitor can be employed to form geodate delivery vehicles in a desired size range.

In a preferred embodiment the geodate delivery vehicles of the present invention further comprise and aggregation inhibitor. In one embodiment, an aggregation inhibitor is employed to obtain geodate delivery vehicles of a desired size. The term "aggregation inhibitor," as used herein, refers to an agent that inhibits aggregation of a geodate delivery vehicle with or without a lipid strata and with or without an emulsion. The aggregation inhibitor typically is present at least on the surface of the geodate delivery vehicle, and may only be present on the surface of the geodate delivery vehicle (e.g., when the aggregation inhibitor is introduced after precipitation). Aggregation inhibitors can be added before, after, or during geodate delivery vehicle formation. Aggregation inhibitors work in part by modifying the surface characteristics of the geodate delivery vehicle such that aggregation is inhibited. Aggregation can be inhibited, for example, by steric bulk and/or a change in the nature of the geodate delivery vehicle structure, e.g., a change in the surface hydrophobicity and/or surface charge. The aggregation inhibitor can be added at any point in the manufacture (e.g., to pre-empt aggregation), and/or after manufacture (e.g., to stabilize the precipitate size and/or disaggregate precipitates).

In a preferred embodiment, the precipitates of the present invention include one or more aggregation inhibitors. The aggregation inhibitor can be added prior to, during, and/or after precipitation. The type and/or amount of aggregation inhibitor can be adjusted to obtain a desired precipitate size and/or distribution. Additionally or alternatively, aggregation inhibitor(s) can be used to stabilize precipitate size and/or size distribution such that aggregation of precipitates is minimized or eliminated.

Suitable aggregation inhibitors that can be employed in accordance with the present invention, include but are not limited to at least one of the following: casein, κ-casein, milk, methylcellulose, ethylcellulose, propylcellulose, hydroxycellulose, hydroxymethyl cellulose, hydroxyethyl cellulose, hydroxypropyl cellulose, hydroxypropylmethyl cellulose, polyvinyl pyrrolidone, carboxymethyl cellulose, carboxyethyl cellulose, pullulan, polyvinyl alcohol, sodium alginate, polyethylene glycol, polyethylene oxide, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, carrageenan, carnauba wax, shellac, latex polymers, milk protein isolate, soy protein isolate, whey protein isolate and mixtures thereof.

A preferred aggregation inhibitor is casein. Casein is a highly phosphorylated, calcium binding protein. Without wishing to be bound to any particular theory, it is believed that calcium mediates an interaction between negatively charged lipid (e.g., PS) and casein, thereby changing the surface properties of precipitates such that aggregation is inhibited. Another preferred aggregation inhibitor is milk and other milk products such as Half and Half, cream, etc. Another preferred aggregation inhibitor is methylcellulose.

More than one aggregation inhibitor may be employed in the compositions of the invention. For example, both milk and methylcellulose may be used as an aggregation inhibitor.

In one embodiment, the precipitate compositions of the invention include an aggregation inhibitor to lipid ratio of between about 0.5:1 to about 4:1 by weight. Preferably, the aggregation inhibitor to lipid ratio is about 1:1. A person of ordinary skill in the art will readily be able to determine the amount of aggregation inhibitor needed to form precipitates of the desired size with no more than routine experimentation.

Pharmaceutical formulations incorporating the delivery vehicles of the present invention can be of solid form including tablets, capsules, pills, bulk or unit dose powders and granules or of liquid form including solutions, fluid emulsions, fluid suspensions, semisolids and the like. This is particularly true using vehicles including a lipid strata, as the crystalline structure protects the agent from its environment and vice versa. In addition to the active ingredient, the formulation would comprise suitable art-recognized diluents, carriers, fillers, binders, emulsifiers, surfactants, water-soluble vehicles, buffers, solubilizers and preservatives.

Pharmaceutical formulations incorporating the delivery vehicles of the present invention can be of liquid or semi-liquid form including food products, such as therapy or nutrient drinks, yogurt, milk, salad dressing, moist animal food, and the like. The stable emulsions of the present invention can be directly added to such formulations.

An advantage of the vehicles of the present invention is the stability and safety of the composition, particularly when soy-based lipids are employed. Thus, the geodate delivery vehicles can be administered orally or by instillation without concern, as well as by the more traditional routes, such as topical, subcutaneous, intradermal, intramuscular and the like. Direct application to mucosal surfaces is an attractive delivery means made possible with the delivery vehicles.

The skilled artisan can determine the most efficacious and therapeutic means for effecting treatment practicing the instant invention. Reference can also be made to any of numerous authorities and references including, for example, "Goodman & Gilman's, The Pharmaceutical Basis for Therapeutics", (6th Ed., Goodman, et al., eds., MacMillan Publ. Co., New York, 1980).

The geodate delivery vehicles of the instant invention also serve as excellent means for delivering fragile cargo moieties to a host. Such cargo moieties include nutrients, vitamins such as vitamins A, D, E or K, co-factors, enzymes, fatty acids such as polyunsaturated forms, minerals including divalent cations such as calcium, magnesium, zinc, iron or barium, flavors and the like. Because the cargo moiety is contained within the vehicle, in a non-aqueous environment, the agent essentially is stabilized and preserved. Hydrophobic molecules can be made part of the geodate delivery structure, with little difficulty as the lipid monolayer of the present invention will form about a hydrophobic domain.

The geodate delivery vehicles can be particularly advantageous for delivering agents to food and drinks to be consumed by humans or other animals. For example, dog and cat food can include the vehicles of the present invention to stably deliver vitamins, flavoring agents, minerals or other nutrients, as well as medications, e.g., allergy medications. Similarly, the geodate delivery vehicles of the present invention can be added to pet or domestic animal feed, such as fish food and food for fowl, cattle, and horses. The vehicles can be added at any step of the preparation. For example, the vehicles can be added at any point in the methods described in WO 02/44026, incorporated herein by this reference. Similarly, the compositions and methods of the invention can be employed in food or drink to be consumed by humans, e.g., in a nutrient bar or drink, cereals, breads, and snack food. Accordingly, the preparations of the invention allow for the production of stable, convenient preparations of micronutrients in processed foods, such as fast foods. Typically, potentially beneficial micronutrients, e.g., omega fatty acids and antioxidants, can be destroyed during food manufacture and storage. The delivery vehicles of the invention protect micronutrients and other cargo moieties, thus increasing the nutritional and/or medicinal value of the food.

Because of their increased stability, the compositions and methods of the present invention are particularly useful in foods that are baked or cooked, such as cakes, muffins, pasta noodles, soups, cereals, chips, candy and cookies. In a preferred embodiment, the compositions are used in candy, such as candy bars, e.g., chocolate bars. For example, omega fatty acid-geodes can be incorporated into a chocolate bar.

The geodate delivery vehicles can be added to food items, e.g., fast food products, in the crystallized or emulsion form at any stage of the manufacturing process. The food item can be an animal food item, a human food item, a nutrient bar, a snack food, a beverage, a domesticated animal food, a fish food, a poultry feed, a pet food, a dog food or a cat food They preferably are added at a stage where the integrity of the delivery vehicle is maintained until ingestion, or final preparation of the food product by the consumer. Another alternative, however, can be to use the vehicles to maintain the stability of the agent until incorporation into the product, so activity can be maintained during storage and shipping. Yet another alternative is to deliver the vehicles themselves to consumers or professionals, for direct addition to food products, e.g., medicament, nutrient crystals, additives, supplements, or emulsions, such that the user can vary the concentration as desired.

The vehicles can also be added to a carrier for use as a topical treatment on the skin. Suitable carriers would remain on the skin for an extended period of time, and be resistant to perspiration or immersion in water. Thus, for example, the vehicles may be added to topical applications of medicaments, moisturizers, deodorants, balms, fragrances, sunscreens, and the like.

Additional examples of formulations that can include the geodate delivery vehicles of the invention include, but are not limited to, hair care products, skin care products, personal care products, personal cleansing products, lotions, fragrances, sprays, perfumes, cosmetics, toothpastes, tooth whiteners, cleaners, bar soap, liquid soap, body wash, baby wash, makeup, hair color, shampoos, conditioners, styling products, balms, creams, solutions, gels and solids. Thus, for example, shampoos, conditioners and the like may contain geodate delivery vehicles loaded with vitamins, moisturizers, perfumes, medications, etc.

The vehicles can also be added to cleansers which do not have direct contact with the skin. These formulations would be advantageous for, i.e., the incorporation of perfumes, moisturizers or other such cargo moieties into fabric or for the introduction of an antibacterial agent to dishes. Examples include, but are not limited to, laundry detergent, pre-treating formulations, dryer sheets, fabric softener, and dishwashing detergent.

Geodate delivery vehicles can also be added to paper products for the topical application of cargo moieties to skin. Examples of paper products that can include geodate delivery vehicles of the invention include baby care products, i.e, diapers or baby wipes, tissues, toilet paper, antibacterial or antiperspirant towelettes, napkins, paper towels, bandaids, gauze pads, and feminine hygiene products.

An artisan can determine without undue experimentation the optimal lipid to cargo moiety and/or hydrophobic domain ratios for a specific purpose. Formation of geodate delivery vehicles is monitored readily. Then, the preparation can be administered to the targeted host to ascertain the nature and tenor of the biologic response to the administered composition. It should be evident that the optimized ratio for any one use may range from a high ratio, for example, to minimize the use of a rare cargo moiety, to a low ratio to obtain maximal amount of cargo moiety in the vehicle.

Because the vehicle can accept a large load of cargo moiety, the amount of cargo moiety can vary greatly depending on need.

The present invention also provides a method of manufacturing a geodate delivery vehicle for a cargo moiety. The method generally includes the step of: mixing a lipid, an aqueous solution and a hydrophobic material, such that a geodate delivery vehicle is formed, which includes a lipid monolayer disposed about a hydrophobic domain.

An alternate method of forming a geodate delivery vehicle includes mixing a lipid and a hydrophobic material, e.g., by kneading, such that one or more geodate delivery vehicles are formed. This method can be advantageous, for example, when an aqueous environment is not desired. Fragile cargo moieties are often sensitive to moisture, which can cause decomposition upon prolonged exposure. A non-aqueous method for forming geodate delivery vehicles, therefore, would be desirable At a low lipid to hydrophobic domain ratio, the lipids tend to form micelles in the water; at a higher concentration the lipids will form lipid monolayers about the hydrophobic globule. Preferably, the lipid to hydrophobic domain ratio is between 5:1 and about 10:1.

The method can further include the step of adding a cargo moiety, wherein the cargo moiety associates with the hydrophobic domain. The agent can be added prior to or after emulsifying the mixture to form the lipid monolayer about the hydrophobic domain. Alternatively, the hydrophobic domain may itself be a cargo moiety, e.g., fish oil.

The methods of the invention can include the step of adding a cation to the emulsion to form a lipid strata about a geodate delivery vehicle. The lipid strata can be maintained in the emulsion. Optionally, the method can include the step of extracting the precipitate from the emulsion to form a solid or semi-solid, e.g., a powder. The geodate delivery vehicle can be harvested from the suspension by filtration, centrifugation or other techniques, and dried to a powder. As shown below, the geodates can be extracted from suspension using commercial, large-scale or large batch equipment, e.g., spray dryers or fluid bed dryers. Geodes recovered with such equipment can experience extreme temperatures, e.g., 400° F., for prolonged periods of time without degrading the geode structure or its cargo.

Alternatively, the geodates can be dried using an apparatus which uses high pressure and hot air to form a powder. The high pressure creates a mist from the geodate suspension, which enters a chamber from the top. The hot air enters the camber from the bottom and blows seed crystals into the center of the chamber. When the mist and the seed crystals meet, geodates coat the seed crystal, and powder forms.

Use of the delivery vehicles of the present invention, e.g., geodes, can result in an increase in the amount of active ingredient delivered versus that which can be achieved with conventional food or drug preparations. For example, the delivery vehicles of the present invention can result in a 20%, 40%, 50%, 60%, 100%, 200% ... 1000% ... 10,000% increase in the active (undegraded) ingredient delivered versus use of the cargo directly in the preparation of the drug, food, beverage, etc.

FIG. 1 illustrates an exemplary method of manufacturing a geodate delivery vehicle in accordance with the present invention. The lipid (e.g., a phospholipid) is represented in liposomes as open rings, and individually and in lipid monolayer arrangements as hairpin-like structures indicating the hydrophilic head and hydrophobic tail portions of a typical phospholipid. The hydrophobic domains (e.g., oil droplets), are represented by shaded circles. Lipid strata is represented with hatching. The phospholipid and oil droplets are emulsified to create a stable emulsion that includes liposomes as well as geodate delivery vehicles that each include a lipid monolayer disposed about a droplet of oil. Oil droplets have phospholipid imbedded in their surface. Most likely the hydrophobic acyl chains of the phospholipid are within the oil. This results in the oil droplets having a hydrophilic surface due to the coating of phospholipid head groups. This results in a stable emulsion. A cation is added (e.g., calcium), and the liposomes collapse into a strata of alternating liposome bilayer and calcium layers. In FIG. 1, several crystals are depicted, each one capturing several geodate delivery vehicles. Optionally, the crystals can be removed from the suspension (not shown).

Figure 3:
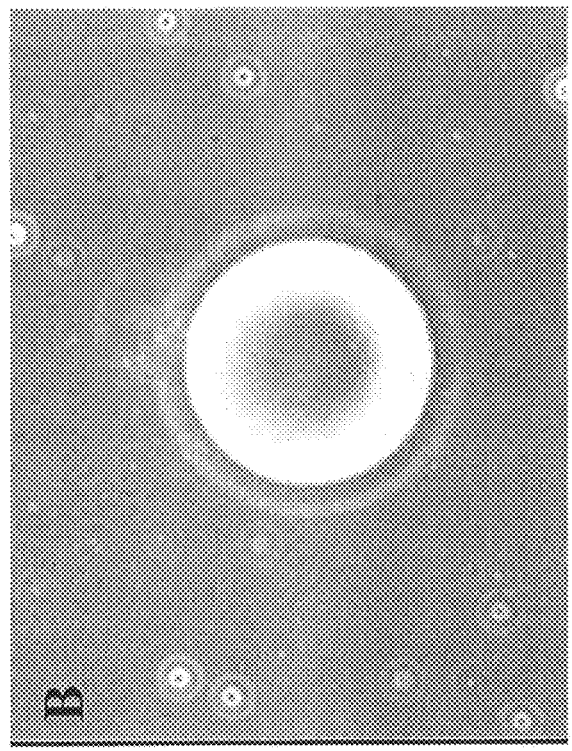
FIGS. 3A-B are two images of exemplary geodate delivery vehicles that include a DOPS monolayer disposed about Amphotericin B in olive oil.
Figure 3:
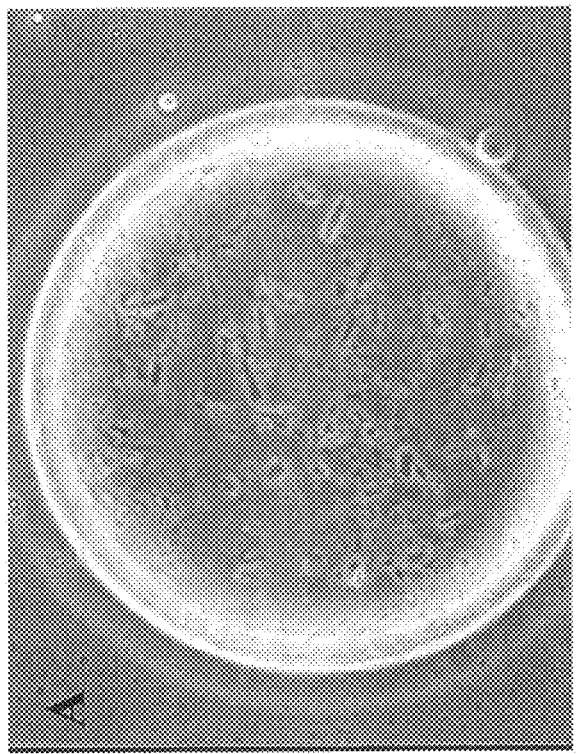
Figure 4:
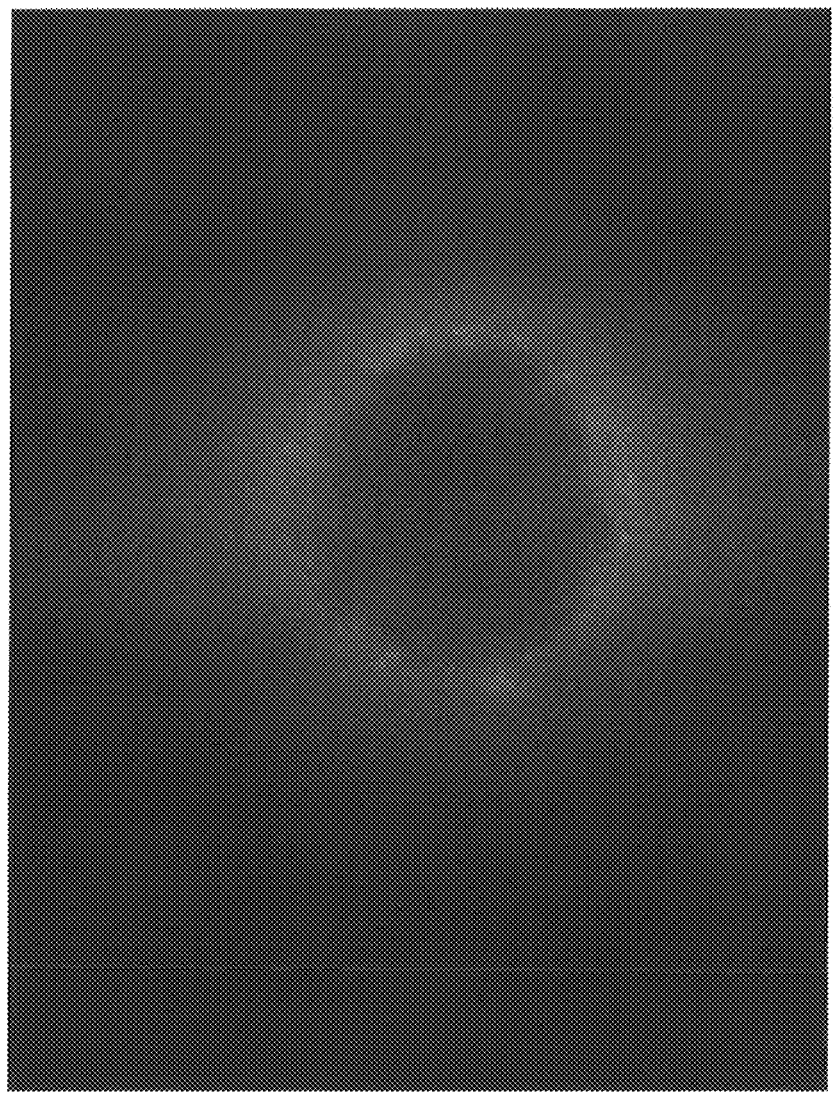
FIG. 4 is an image of a DOPS geodate delivery vehicle that includes a DOPS monolayer about fluorescent Amphotericin B interacting with olive oil.
Figure 5:
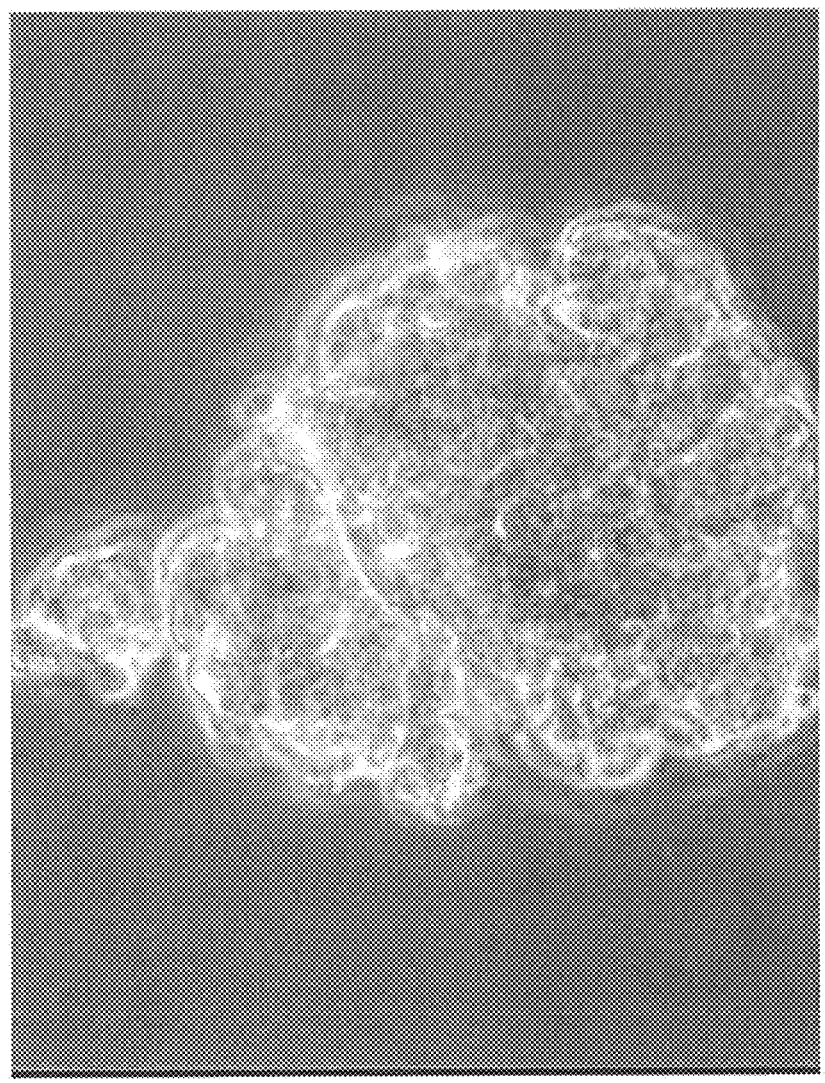
FIGS. 5 and 6 are images of a lipid strata encrusting olive oil, where the lipid includes Rhodamine-labeled DOPS.
Figure 6:
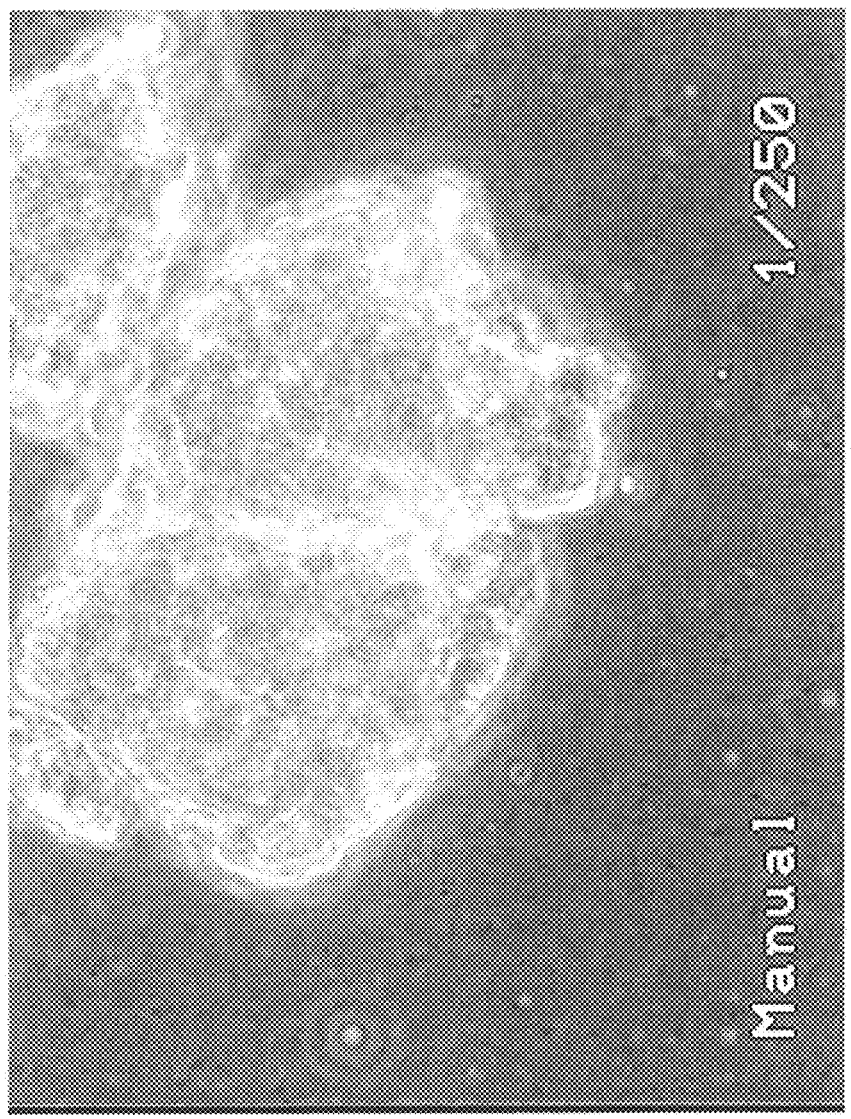
Figure 7:
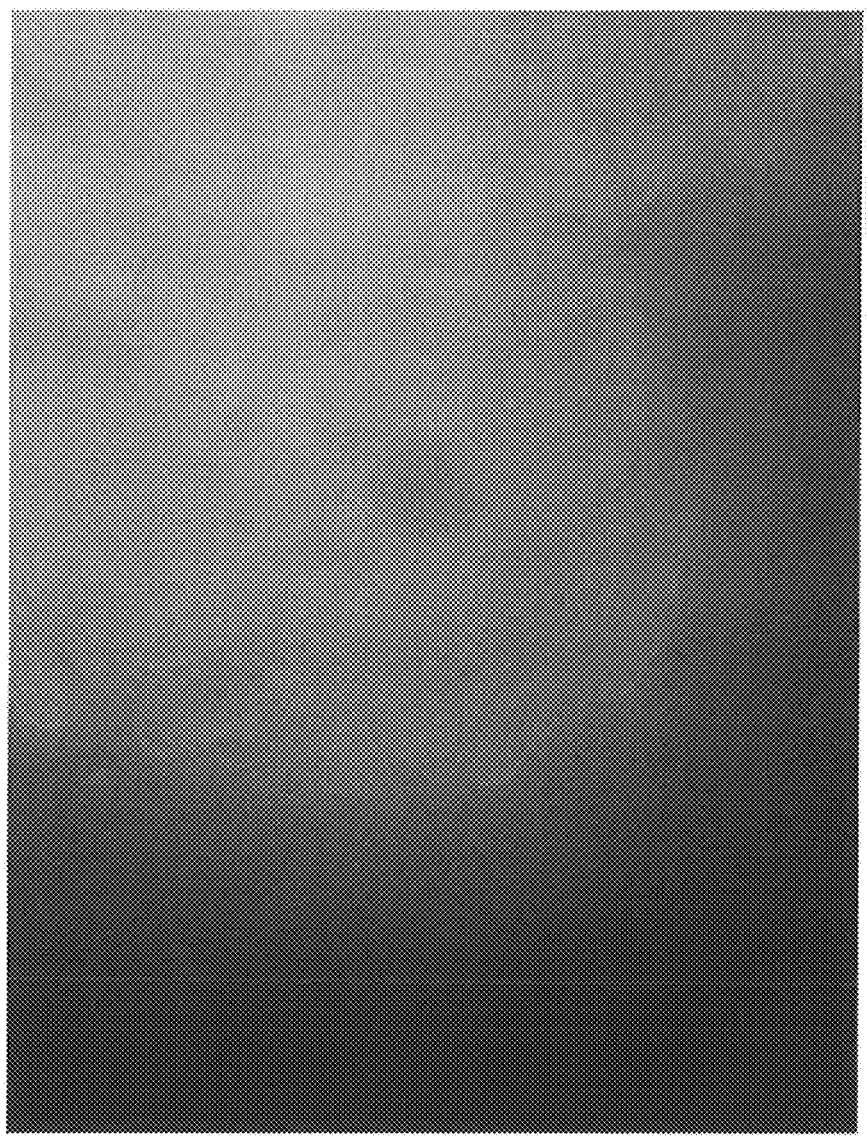
FIGS. 7 and 8 are images of a geodate delivery vehicle including a fluorescent DOPS monolayer disposed about olive oil, after release from a lipid strata.
Figure 8:

To further illustrate the present invention, FIGS. 2A-D include four images of DOPS and olive oil interacting in an aqueous buffer. FIGS. 3A and B are two images of geodate delivery vehicles including a DOPS monolayer disposed about Amphotericin B in olive oil. FIG. 4 is an image of a DOPS geodate delivery vehicle that includes a DOPS monolayer about fluorescent Amphotericin B interacting with olive oil. FIGS. 5 and 6 are images of a lipid strata encrusting olive oil, where the lipid is Rhodamine-labeled DOPS. FIGS. 7 and 8 are images of a geodate delivery vehicle that includes a fluorescent DOPS monolayer disposed about olive oil, after a lipid strata formed with calcium was removed with a chelating agent.

The natural composition of the preparations of the present invention reduces the risks associated with other delivery methods such as methods using unnatural chemicals or methods using infectious viral vector systems. The preparations are manufactured relatively easily and inexpensively, and are compatible with a wide range of cargo moieties. The preparations can be delivered orally in a suspension or vehicle such as a food vehicle (e.g., liquid or solid food items). Thus, the preparations of the present invention may eliminate the need for painful and difficult injections. Moreover, the preparations are not restricted to prescription drugs, but may also be used to deliver over-the-counter medication or other agents, such as vitamins, minerals or other nutrients.

An example of such cargo moieties are omega-3 fatty acids, which are found mainly in fish oils and other fish products. Omega-3 fatty acids have been implicated in increased disease resistance and fertility in animals, and they are shown to have a significantly positive effect on cholesterol and overall cardiovascular health in human beings. See, for example, Daviglus et al. N Engl J. Med. 336: 1046-1053 (1997). One of the complications of incorporating them directly into food, however, is their noticeable odor and taste.

The present invention provides a means for masking flavors and odors, such as those associated with omega-3 fatty acids, by encapsulation within a lipid strata. For example, omega-3 fatty acid-geodes have been added to beverages such as soy milk, milk, liquid yogurt, grapefruit juice, orange juice, smoothies, sports drinks, soft drinks, tea, coffee, and iced coffee. In each case, there was no alteration in taste or odor of the beverage, i.e., the characteristic fish odor of the omega-3 fatty acid was not discernable. Similarly, omega-3 fatty acid geodes can be used in goods that are then baked or cooked, such as cakes, muffins, pasta noodles, soups and cookies without alteration in taste or odor.

The present invention is also particularly advantageous for the delivery of unstable cargo moieties such as beta-carotene. Beta-carotene acts as an antioxidant by quenching singlet oxygen and other free radicals. Unfortunately beta-carotene and other carotenoids are highly susceptible to oxidation prior to incorporation into the body. This phenomenon is observed as a bleaching of the deep orange color. Britton, FASEB J. 9: 1551-1558 (1995).

Figure 18:
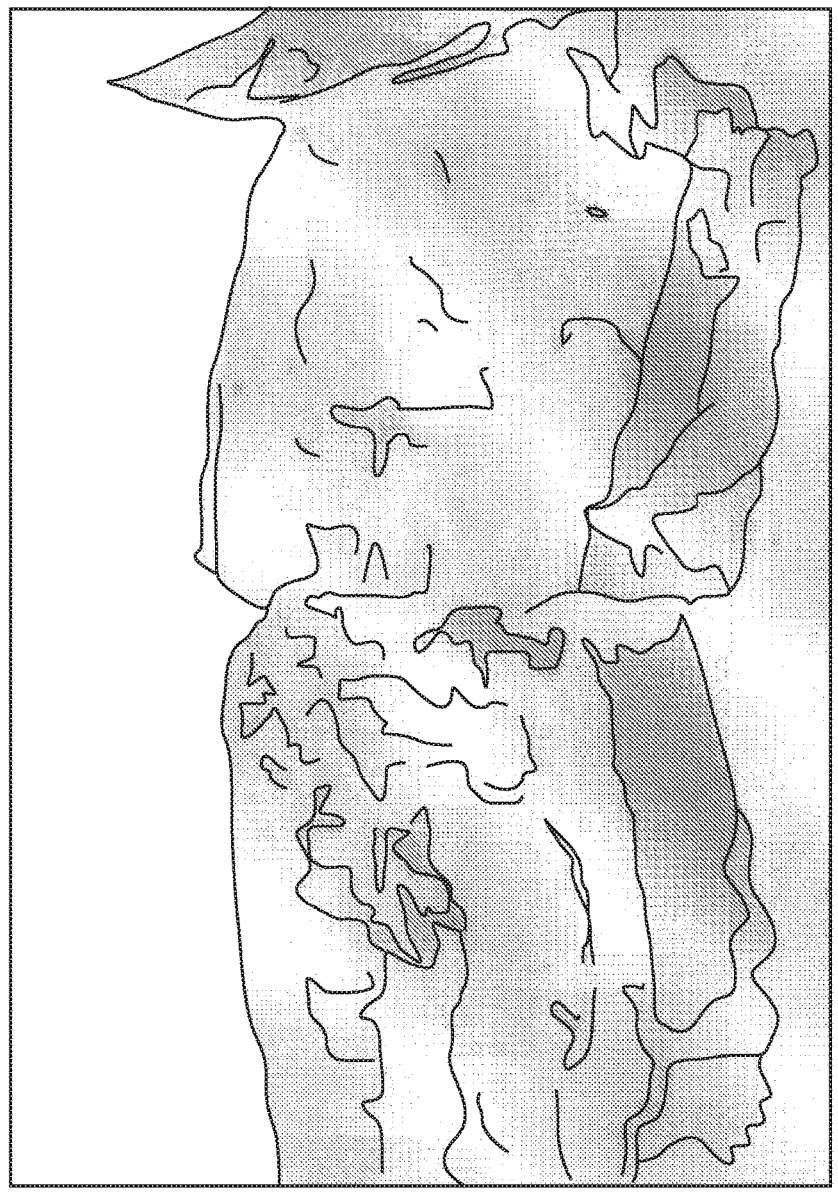
FIG. 18 is an image of a muffin containing beta-carotene geodes.

The present invention provides beta-carotene with an oxygen-free environment for storage before use. Surprisingly, the beta-carotene maintained activity even after exposure to extreme temperatures and pressures which normally would degrade it. FIG. 18 is an the image of beta-carotene geodes contained within muffins baked at approximately 350° F. for about twenty minutes. The activity is indicated by the red-orange color observed in the muffins. Additionally, beta-carotene geodes can be incorporated into other baked or cooked items and beverages.

In another embodiment, the geodate delivery vehicles can be employed to deliver nonsteroidal anti-inflammatory drugs (NSAIDS), typically used to treat inflammation, muscle strains, and high fever. NSAIDS function by inhibiting cyclooxygenase-1 (COX1) and cyclooxygenase-2 (COX2). COX1 enzymes are responsible for protecting the lining of the stomach and COX2 enzymes are responsible for the production of prostaglandins, which are important in the inflammatory process. Unfortunately, commercially available preparations of NSAIDS are active against both COX1 and COX2, and therefore have unwanted side effects such as ulcers, upset stomach or nausea.

Ibuprofen and naproxen are two of the more widely used and well known NSAIDS commonly used to relieve pain and fever. Low doses of ibuprofen are used to control pain, but inflammation can not be regulated without a higher dosage, which often causes stomach upset, diarrhea, dizziness, drowsiness, gas, heartburn, or headache, and occasionally more serious side effects such as kidney toxicity or jaundice. Naproxen is used to treat both pain and inflammation; however, diarrhea, constipation, dizziness, drowsiness, gas, heartburn, nausea, vomiting, headache, increased susceptibility to sunburn and ringing in the ears are common side effects. A delivery vehicle, therefore, is needed to successfully deliver such NSAIDs to the macrophage without unwanted side effects.

Macrophages are important in the uptake of bacteria, fungi and parasites, and also play an important role in the inflammatory response. In addition to performing phagocytosis, macrophages have the potential of being activated, a process that results in increased cell size, increased levels of lysosomal enzymes, more active metabolism, and greater ability to phagocytose and kill ingested microbes. After activation, macrophages secrete a wide variety of biologically active products that, if unchecked, result in tissue injury and chronic inflammation. One of the secreted products, nitric oxide (NO), has come into the forefront as a mediator of inflammation.

Nitric oxide (NO) produced by inducible NOS plays an important role in inflammation, killing of bacterial pathogens, and tissue repair. NO formation increases during inflammation (i.e., in rheumatoid arthritis, ulcerative colitis, and Crohns disease), and several classic inflammatory symptoms, (i.e., erythema and vascular weakness) are reversed by NOS inhibitors. Nitric oxide has also been recognized as playing a versatile role in the immune system. It is involved in the pathogenesis and control of infectious diseases, tumors, autoimmune processes and chronic degenerative diseases.

The mechanism of action and side effects of NSAIDS, such as ibuprofen and naproxen, are explained in part by the generation of NO from iNOS Inhibition of iNOS expression and NO production by employing the geodate delivery vehicles of the present invention could be a way to therapeutically decrease the inflammatory actions of these drugs.

Another aspect of the present invention is a method of administration of the preparations of the present invention. Accordingly, the present invention provides a method of treating a subject that can benefit from the administration of a cargo moiety, including the step of administering a geodate delivery vehicle comprising a cargo moiety to a subject. The preparations of the present invention can be used to treat fungal infections (e.g., by delivery of a antifungal agent such as Amphotericin B), to treat or prevent HIV infection (e.g., by delivery of a vaccine or a peptide to induce cellular immunity), to treat macular degeneration (e.g., by delivery of a nutriceutical), to treat inflammation (e.g., by delivery of an anti-inflammatory), to treat bacterial infections (e.g., by delivery of antibiotics), and to provide nutrients (e.g., by delivery of vitamins, minerals or oils).

Accordingly, the present invention provides for both prophylactic and therapeutic methods of treating a subject at risk of (or susceptible to) a disorder or having a disorder which can be treated with one or more cargo moiety.

"Treatment", or "treating" as used herein, is defined as the application or administration of a therapeutic agent (e.g., NSAIDS) to a patient, or application or administration of a therapeutic agent geode of the invention to an isolated tissue or cell line, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease. "Treated," as used herein, refers to the disease or disorder being cured, healed, alleviated, relieved, altered, remedied, ameliorated improved or affected.

The methods of the present invention include methods of administering a cargo moiety to a subject or host, wherein the cargo moiety is associated with a geodate delivery vehicle of the invention. The geodate delivery vehicles of the present invention may be administered orally, nasally, topically, intravenously, transdermally, buccally, sublingually, rectally, vaginally or parenterally.

The present invention provides a method for treating a subject that would benefit from administration of a composition of the present invention. Any therapeutic indication that would benefit from a cargo moiety, e.g., a drug or nutrient, can be treated by the methods of the invention. Accordingly, the present invention provides methods of treating a subject at risk for or having a disease or disorder which can be treated with, for example, a protein, a small peptide, an antiviral, an anesthetic, an anti-infectious, an antifungal, an anticancer, an immunosuppressant, a steroidal anti-inflammatory, a non-steroidal anti-inflammatory, an antioxidant, an antidepressant which can be synthetic or naturally derived, a substance which supports or enhances mental function or inhibits mental deterioration, an anticonvulsant, an HIV protease inhibitor, a non-nucleophilic reverse transcriptase inhibitor, a cytokine, a tranquilizer and/or a vasodilatory agent. The method includes the step of administering to the subject a composition of the invention, such that the disease or disorder is treated. The disease or disorder can be, e.g., inflammation, pain, infection, fungal infection, bacterial infection, viral infection, parasitic disorders, an immune disorder, genetic disorders, degenerative disorders, cancer, proliferative disorders, obesity, depression, hair loss, impotence, hypertension, hypotension, dementia, senile dementia, or malnutrition.

The geodate delivery vehicles of the instant invention can be used to treat a variety of inflammations, including headache, arthritis, rheumatoid arthritis, osteoarthritis, acute gout, acute or chronic soft tissue damage associated with, e.g., a sports injury, tennis elbow, bursitis, tendonitis, acute or chronic back pain, such as a herniated disc, carpal tunnel syndrome, glomerulonephritis, carditis, ulcerative colitis, asthma, sepsis, and plantar fasciitis. The geodate delivery vehicles of the invention can also be used to relieve pain resulting from surgery or other medical procedure. The geodate delivery vehicles of the instant invention can further be used to treat a variety of fungal infections, including candida, e.g., yeast infection, tinea, e.g., Athlete's foot, pityriasis, thrush, cryptococcal meningitis, histoplasmosis, and blastomycosis.

The geodate delivery vehicles of the instant invention can also be used to treat a variety of bacterial infections, including but not limited to moderate to severe lower respiratory tract infections, skin infections, biliary tract infections, bone infections, antibiotic prophylaxis, pseudomembraneous enterocolitis, central nervous system infections (e.g., meningitis and ventriculitis), intra-abdominal infections (e.g., peritonitis), pneumonia, septicemia, soft tissue infections, neutropaenic sepsis, joint infections, infective endocartidis, and urinary tract infections.

Exemplary bacteria that can be treated with the antibiotic preparation of the present invention include, but are not limited to, *Staphylococcus aureus, Staphylococcus epidermidis, Streptococcus pyogenes, Streptococcus pneumoniae, Streptococcus* Group D, *Clostridium perfringens, Haemophilus influenzae, Escherichia coli, Pseudomonas aeruginosa*, and *Klebsiella pneumoniae*.

The above methods can be employed in the absence of other treatment, or in combination with other treatments. Such treatments can be started prior to, concurrent with, or after the administration of the compositions of the instant invention. Accordingly, the methods of the invention can further include the step of administering a second treatment, such as for example, a second treatment for the disease or disorder or to ameliorate side effects of other treatments. Such second treatment can include, e.g., radiation, chemotherapy, transfusion, operations (e.g., excision to remove tumors), and gene therapy. Additionally or alternatively, further treatment can include administration of drugs to further treat the disease or to treat a side effect of the disease or other treatments (e.g., anti-nausea drugs).

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market.

More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment according to that individual's drug response genotype. Pharmacogenomics allows a clinician or physician to target prophylactic or therapeutic treatments to patients who will most benefit from the treatment and to avoid treatment of patients who will experience toxic drug-related side effects.

The language "therapeutically effective amount" is that amount necessary or sufficient to produce the desired physiologic response. The effective amount may vary depending on such factors as the size and weight of the subject, or the particular compound. The effective amount may be determined through consideration of the toxicity and therapeutic efficacy of the compounds by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

In yet another aspect, the invention provides kits or otherwise packaged geodate delivery vehicles. In one embodiment, the invention provides a packaged geodate delivery vehicle including: a geodate delivery vehicle of the invention packaged with instructions for adding the vehicle to a food, beverage or personal care product. In another embodiment, the packaged geodate delivery vehicle is packaged with instructions for incorporating a cargo moiety into the geodate delivery vehicle.

This invention is further illustrated by the following examples which should not be construed as limiting.

EXAMPLES

Materials and Methods

Imaging of Geodes

Phase contrast light microscopy and confocal microscopy (Olympus) were used to image suspensions, cochleates, and geodes, with and without the aid of fluorescence, which can be used, e.g., in the future study of cellular uptake and intracellular distribution of fluorescently labeled geodes and cargo moieties. Confocal microscopy is particularly advantageous as it is a 3-dimensional digital imaging device that can be used to effectively view slices of cell culture.

Cell Lines and Culture Conditions

Mouse macrophage J774A.1 cell line was obtained from ATCC. The macrophage cells were grown in monolayers in humidified air with 5% $CO_2$ at 37° C. in 60 $mm^2$ Petri dishes (Corning) containing 5 mL of DMEM supplemented with 10% FBS. For experiments, cells were harvested by scraping and were seeded into 96-well plates at a density of $5 \times 10^5$ cells.

Example 1

A Lipid Monolayer Preparation of a Cargo Moiety

In a first vessel, a hydrophobic composition was prepared by vortexing dried Amphotericin B (fungal agent) and rhodamine (a fluorescent marking agent) with olive oil until the amphotericin and the rhodamine were integrally mixed with the olive oil. In a separate vessel, dried lipid was vigorously mixed in water to obtain a suspension of liposomes in water. The hydrophobic composition was then added to two portions of the liposome suspension in lipid-to-oil ratios of about 10:1 and about 5:1, and vigorously mixed to form stable emulsions. Inspection of both emulsions under a microscope revealed the formation of the hydrophobic composition encapsulated with a lipid monolayer and liposomes (FIGS. 2A-D, 3A-B and 4 depict similar emulsions). The emulsions were stable and the hydrophobic domain did not coalesce. Such a stable emulsion is illustrated in FIG. 1, wherein the stable emulsion includes geodate delivery vehicles that include lipid monolayers formed about the hydrophobic domains (dark shading), and liposomes.

Example 2

Lipid Monolayer Preparation Cargo Moiety Trapped in a Lipid Strata

Calcium was added to the emulsions of Example 1. A crystalline structure was observed to form about the lipid monolayer. The crystalline structure is believed to include the calcium and liposomes. Each crystal enveloped several encapsulated hydrophobic domain as depicted schematically in FIG. 1. (FIGS. 5 and 6 depict similar structures).

Example 3

Release of Lipid Monolayer Preparation from Strata

EDTA was added to the emulsion of Example 2. The crystal structure was observed to deteriorate such that the encapsulated domain remained, no longer encrusted by the crystalline structure. (FIGS. 7 and 8 depict similar emulsions).

Example 4

Figure 10:
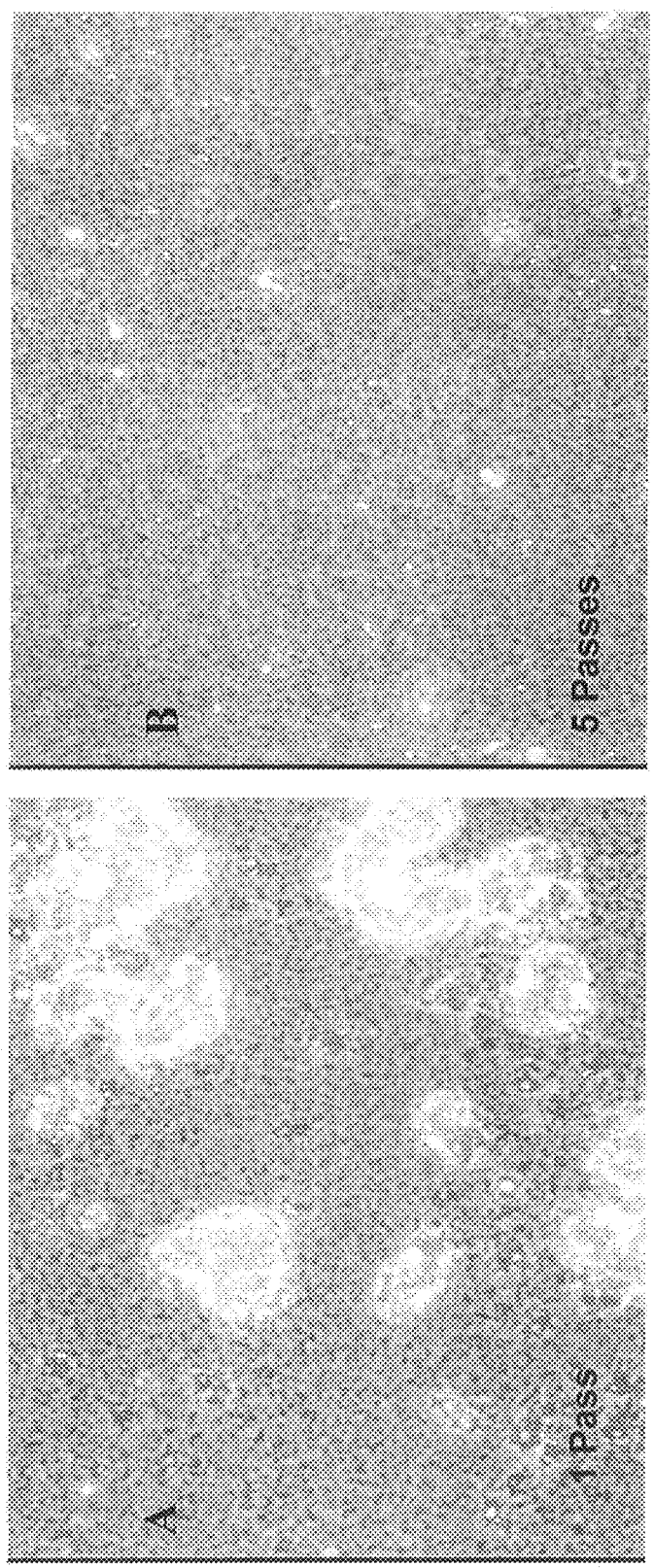
FIGS. 10A and B are two images of a stable beta-carotene/oil/lipid emulsion in aqueous media.
Figure 11:
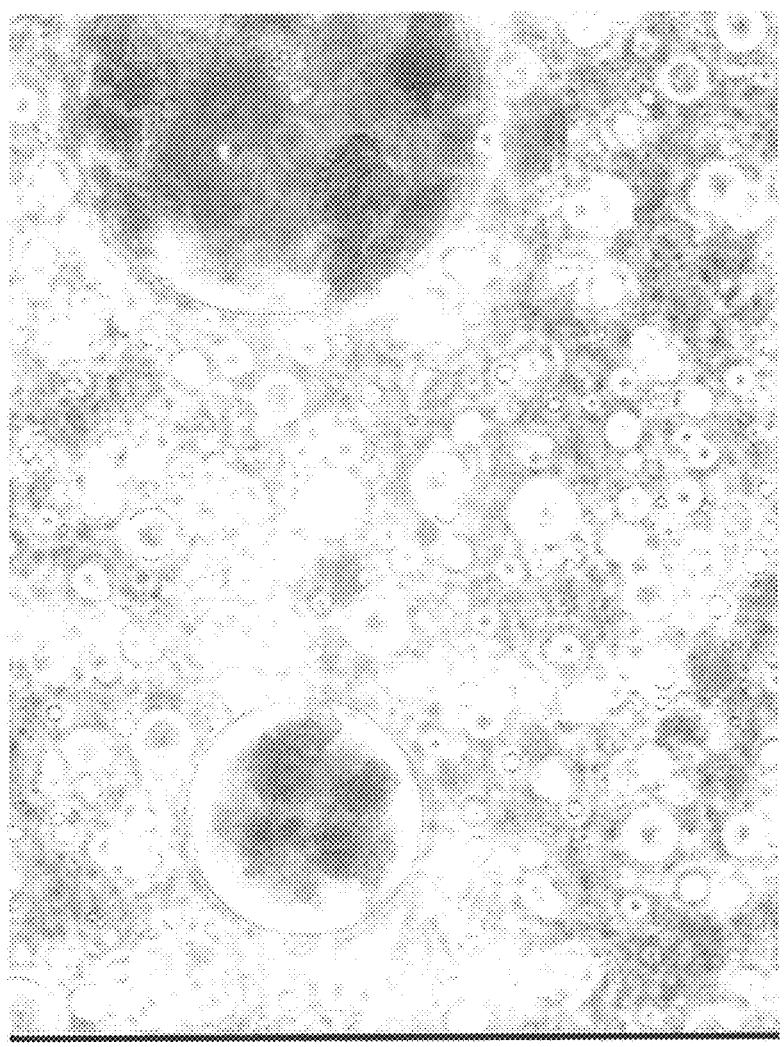
FIG. 11 is an image of a stable emulsion of beta-carotene in soy oil and lipid dispersed in an aqueous environment.

Preparation of Beta-Carotene in Geodate Delivery Vehicle 500 mg of soy phosphatidylserine (PS), 250 mg of 20% beta-carotene in soy oil, 10 mg alpha tocopherol (Vitamin E), and 240 mg of soy oil were weighed into a glass tube. A smooth emulsion was prepared by vigorously mixing the sample at 45° C. Most of the beta-carotene was observed to be incorporated into the oil droplets when examined by light microscopy. FIGS. 10A, 10B and 11 depict stable beta-carotene, oil, and lipid emulsions.

4.5 ml of sterile water was added to the glass tube with vigorous mixing. Microscopic examination revealed a stable emulsion with many different size oil droplets with beta-carotene, a smaller amount of free oil droplets, and many small moving particles.

Figure 9:
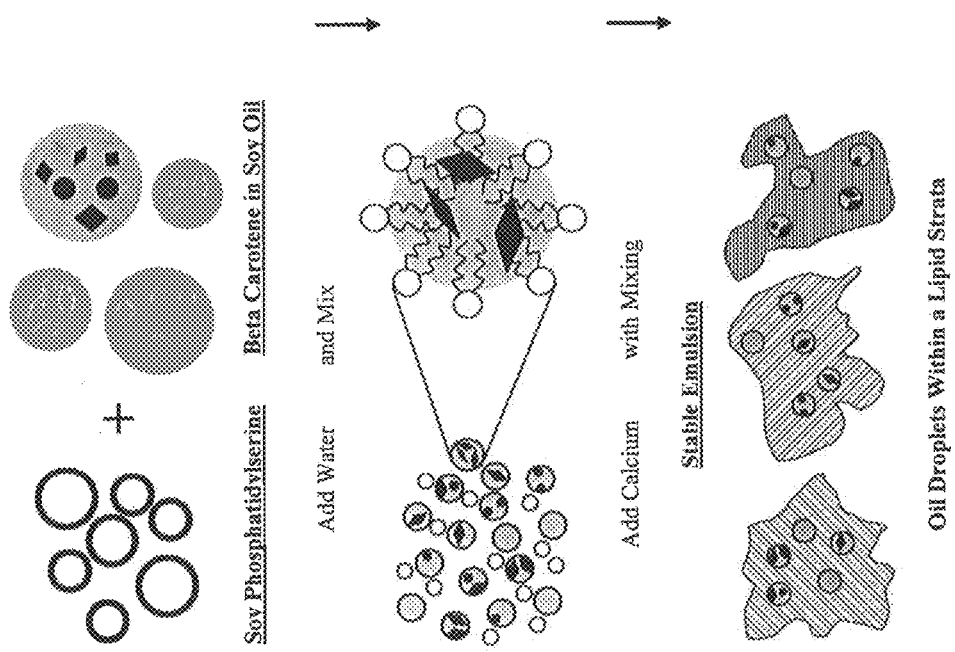
FIG. 9 illustrates another exemplary method of manufacturing a geodate delivery vehicle in accordance with the present invention.

3.3 ml of 0.1 M calcium was added in droplets to the emulsion with vigorous mixing. Examination of this preparation under the microscope revealed vehicle comprising PS monolayers formed about oil droplets containing beta-carotene, captured or encrusted within a lipid strata. FIG. 9 schematically illustrates the method used and the results observed in this experiment.

Example 5

Beta-Carotene Geodate Delivery Vehicles with Casein 12 g of soy phosphatidylserine (PS), 3 g of 20% beta-carotene in soy oil, and 0.2 g alpha tocopherol (Vitamin E), were weighed into a glass tube. A smooth emulsion was prepared by vigorously mixing the sample at room temperature while slowly adding 30-40 ml of sterile water. Most of the beta-carotene was observed to be incorporated into the oil droplets when examined by light microscopy.

4.8 g casein was added to the emulsion, followed by an additional 60-70 ml of sterile water (added dropwise). Microscopic examination revealed a stable emulsion with many different size oil droplets with beta-carotene, a smaller amount of free oil droplets, and many small moving particles.

Figure 12:
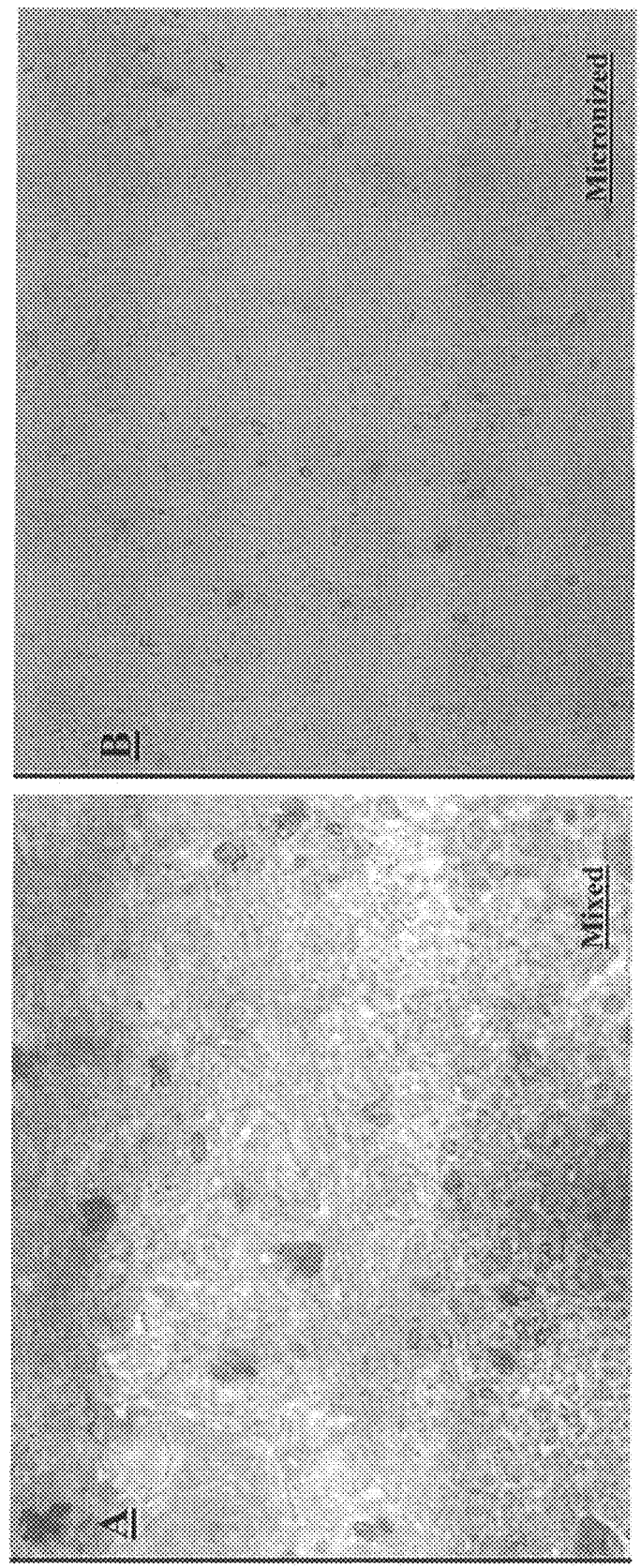
FIGS. 12A and B are two images of beta carotene-oil geodes made in accordance with the present invention.
Figure 13:
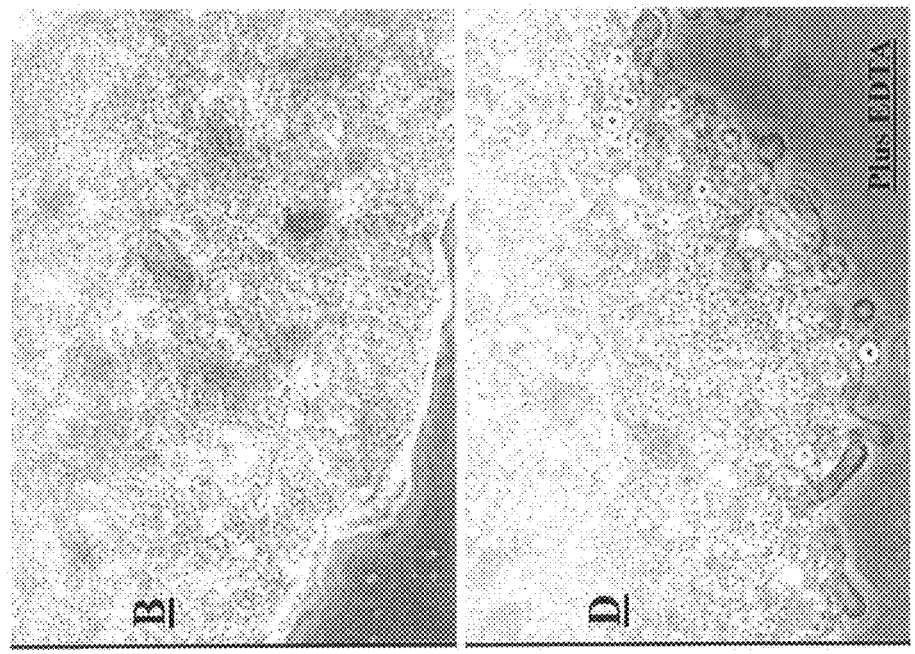
FIGS. 13A-D are images of beta carotene geodes prepared in accordance with the present invention.
Figure 13:
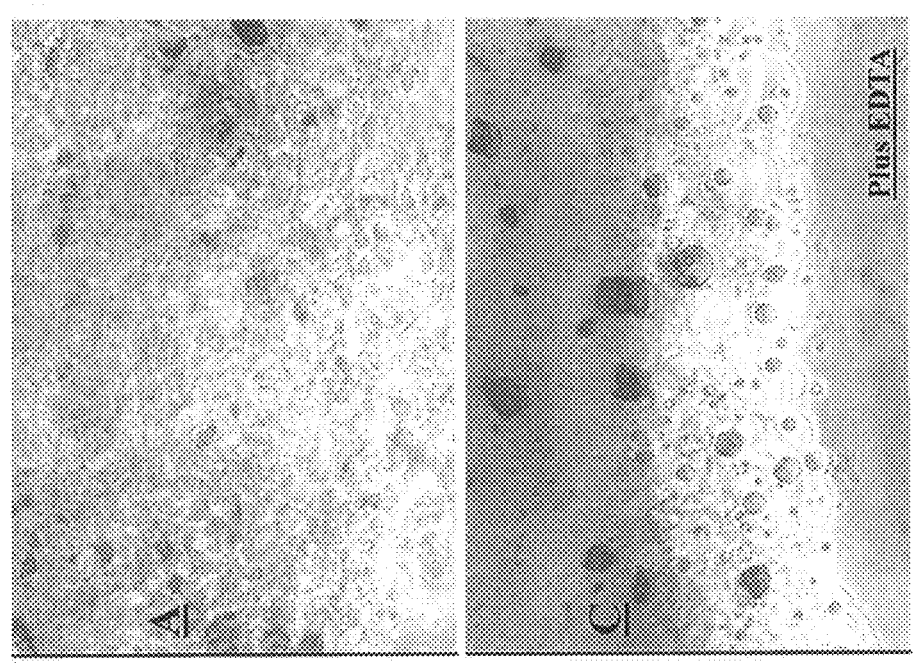

60 ml of 0.5 M calcium chloride was added in droplets to the emulsion with vigorous mixing. Examination of this preparation under the microscope revealed vehicle comprising PS monolayers formed about oil droplets containing beta-carotene, captured or encrusted within a lipid strata. The final composition was calculated as follows Final Composition:
60% phosphatidylserine
24% casein
1% tocopherol
3% beta-carotene
12% soy oil
100 ml sterile water
60 ml 0.5M $Ca^{+2}$ FIGS. 12A and 12B depict beta-carotene geodes before and after micronization. FIGS. 13A and 13B depict beta-carotene geodes in suspension. EDTA can be added to the suspension to release the beta-carotene. FIGS. 13C and 13D depict the suspensions in 13A and 13B, respectively, after the addition of EDTA.

Example 6

Preparation of Fish Oil-Geodate Delivery Vehicles with Casein 12 g of soy phosphatidylserine (PS), 3 g of 30% fish oil, olive oil and 0.2 g alpha tocopherol (Vitamin E), were weighed into a glass tube. A smooth emulsion was prepared by vigorously mixing the sample at 45° C. while slowly adding 30-40 ml of sterile water.

4.8 g casein was added to the emulsion, followed by an additional 60-70 ml of sterile water (added dropwise). Microscopic examination revealed a stable emulsion with many different size fish oil droplets.

60 ml of 0.5 M calcium chloride was added in droplets to the emulsion with vigorous mixing. Examination of this preparation under the microscope revealed vehicle comprising PS monolayers formed about the fish oil droplets, captured or encrusted within a lipid strata. The final compositions were as follows.

Final Composition of Fish Oil-Geodes with Casein
30% fish oil
60% soy phosphatidylserine
10% casein
50 ml sterile water
60 ml 0.1M $Ca^{+2}$
Fish Oil/Casein Geodes with Olive Oil and Tocopherol
30% fish oil (10% olive oil, 1% tocopherol)
60% soy phosphatidylserine
10% casein
50 ml sterile water
60 ml 0.1M $Ca^{+2}$
Fish Oil/Casein Geodes with Olive Oil, Garlic, Curcumin and Tocopherol
30% fish oil (10% olive oil with garlic and curcumin, 1% tocopherol)
60% soy phosphatidylserine
10% casein
50 ml sterile water
60 ml 0.1M $Ca^{+2}$ Example 7

Preparation of Muffins Containing Beta-Carotene Geodes

Beta-carotene geodes were prepared as described in Example 4. These geodes were added to BETTY CROCKER SUPERMOIST white cake mix. The mix was cooked at 350° F. for 20 minutes. The muffins showed clusters of bright orange geodes for at least 12 days subsequent to baking (see FIG. 18).

Example 8

Preparation of Muffins Containing Fish Oil Geodes

Fish oil/olive oil/vitamin E geodes were prepared as described in Example 6. These geodes were added to BETTY CROCKER SUPERMOIST white cake mix. The mix was cooked at 375° F. for about 20 minutes. The muffins showed clusters of light green geodes, and had no noticeable odor for at least 24 hours after baking.

Geodes with only fish oil and without olive oil or vitamin E were prepared as described in Example 6. The geodes were added to the white cake mix and cooked in a microwave until brown (full power, about 45-50 seconds). The muffins had no odor or adverse taste immediately after cooking and after 24 hours.

Example 9

Preparation of Soy Milk Suspension Containing Fish Oil Geodes

Fish oil geodes were prepared as described in Example 6. One teaspoon of fish oil geodes were added to 3 oz. YOPLAIT soymilk. Upon shaking, the fish oil geodes remained in a suspended state. The soy milk exhibited no noticeable odor or taste.

Example 10

Topical Application of Beta-Carotene Geodes

Figure 19:
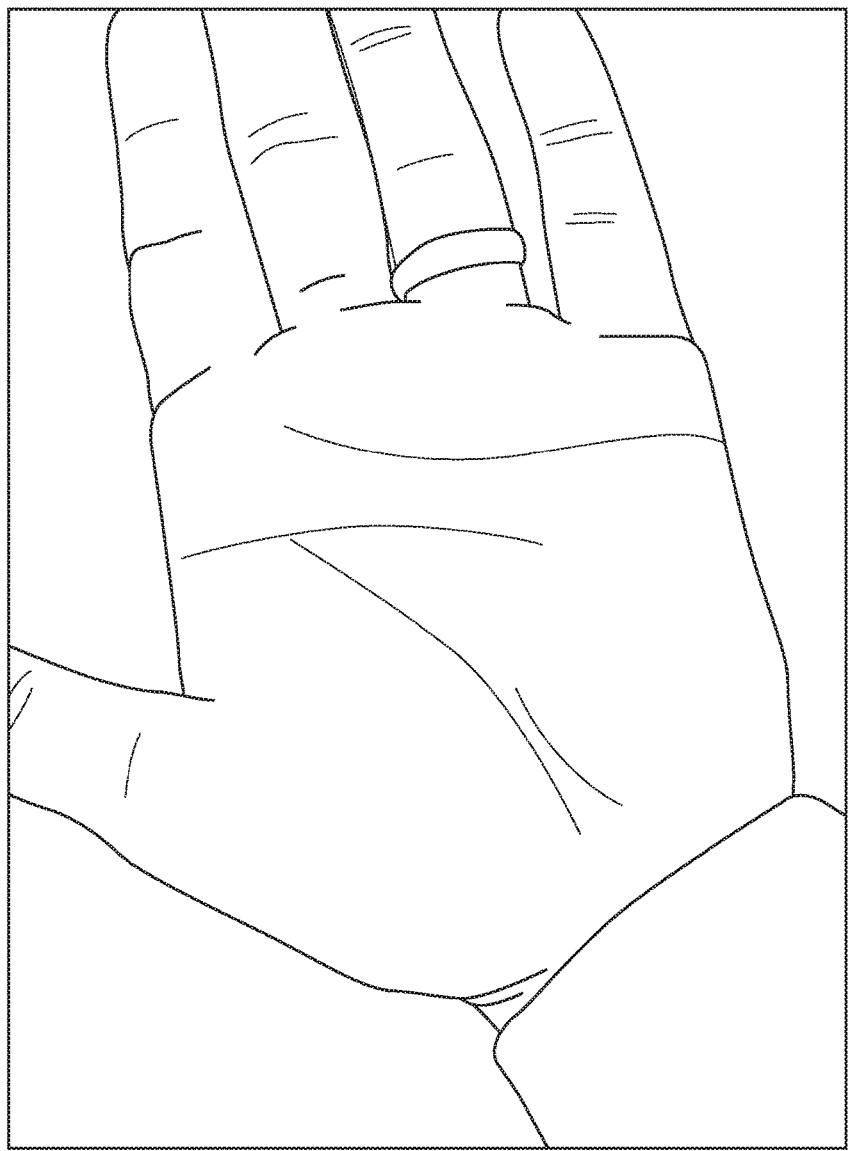
FIG. 19 is an image of beta-carotene geodes applied topically to the palm.

Beta carotene geodes were prepared as described in Example 4, added to petrolatum and applied to the surface of the palm. The coating was resistant to water (see FIG. 19). Without wishing to be bound to any particular theory, it is believed that the geodes may have fused with the stratum corneum of the epidermis.

Example 11

Preparation of Fish Oil Geodes Containing Casein and 5% Tocopherol Using $CaCl_2$ Powder 10 g tocopherol (Vitamin E—Roche) and 50 g fish oil (Roche ROPUFA) were placed in a large KITCHENAID blender and thoroughly mixed by stirring at low speed. 120 g of soy PS (Degussa) was then added to the fish oil/V-E mixture followed by several small aliquots of sterile water. 20 g of casein was then added into the container with fish/V-E emulsion, and sterile water was slowly added with constant low speed stirring until a total of 2000 ml water was added. Microscopic examination showed a stable emulsion with many different size oil droplets and many small moving particles. 35.5 g of calcium chloride powder was added to the container while constantly stirring at low speed. The suspension was subsequently stirred for an additional 30 minutes, after which the sample was transferred into a sterile amber bottle and stored as an emulsion until further use. A spray dryer and a fluid bed dryer have been used to powderize the fish oil geodes.

Final Composition:

| Component | Weight | % before Ca$^+$ | % after Ca$^+$ |
|---|---|---|---|
| fish oil | 50 g | 25% | 21.2% |
| tocopherol | 10 g | 5% | 4.2% |
| soy PS | 120 g | 60% | 50.9% |
| casein | 20 g | 10% | 8.5% |
| CaCl | 35.529 g | | 15.1% |
| sterile water | 2000 mL | | |

Example 12

Preparation of Beta-Carotene Geodes Containing Casein and 0.8% Tocopherol Using CaCl$_2$ Powder 2.6 g tocopherol (Roche) and 39 g of 20% B-carotene in olive oil (Cognis) were placed in a large KITCHENAID blender and thoroughly mixed by stirring at low speed. 156 g of Soy PS (Degussa) was added into the container with B-carotene/vitamin E followed by several small aliquots of sterile water. A smooth emulsion was prepared by vigorously mixing the sample. 62.4 g of casein was then added to the container with the beta-carotene emulsion, followed by slow addition of sterile water until a total volume of 2080 ml was reached. Microscopic examination showed a stable emulsion with many different size oil droplets containing beta-carotene, some free oil droplets, and many small moving particles. 57.3 g of calcium chloride powder was slowly added to the container and the suspension was mixed thoroughly. The suspension was subsequently stirred for an additional 30 minutes at low speed. A 2.0 ml aliquot of the final preparation was placed in a 50 ml sterile tube for HPLC assay. The assay indicated that greater than 90% of the beta carotene in the sample was contained within the geodes. The emulsion was then transferred into a sterile amber bottle until further use.

Figure 15:
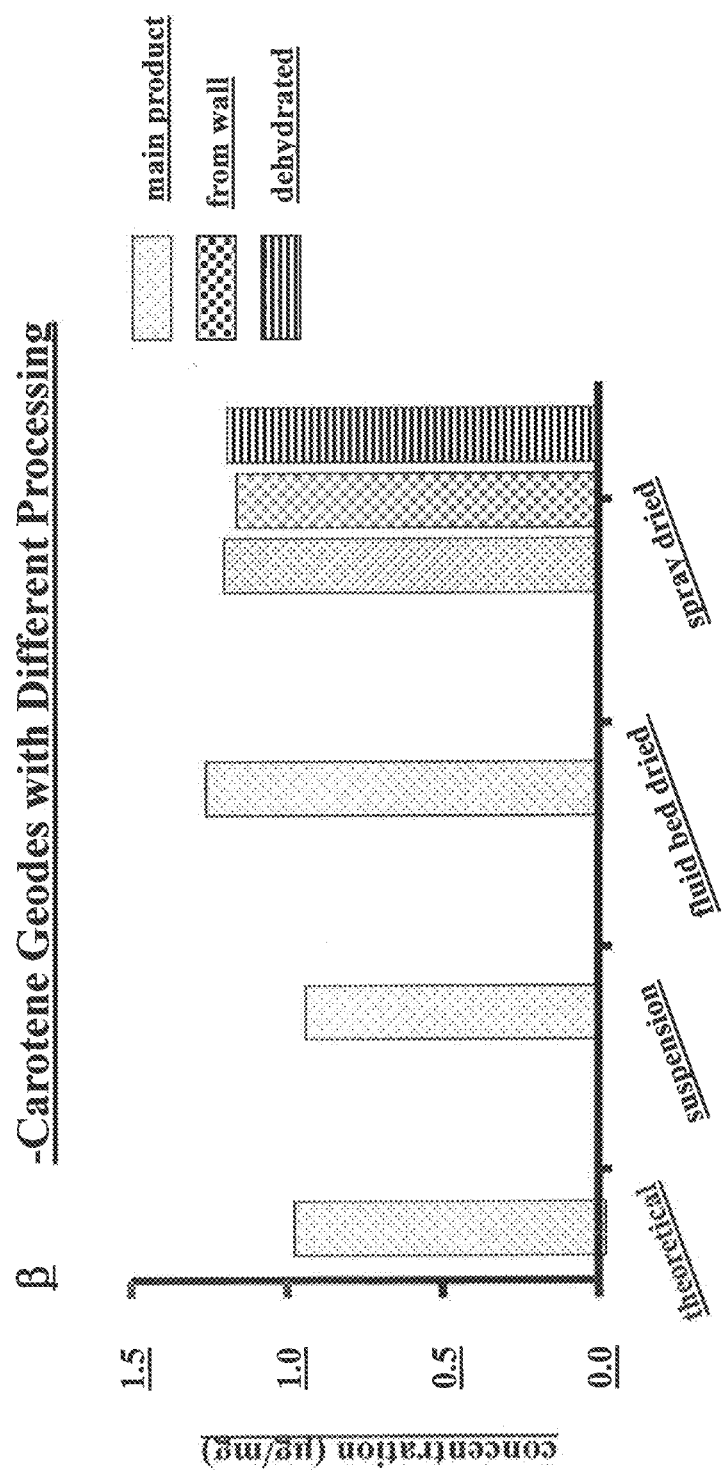
FIG. 15 is a graph showing the stability of beta-carotene geodes in suspension, after spray drying, and after fluid bed drying.
Figure 16:
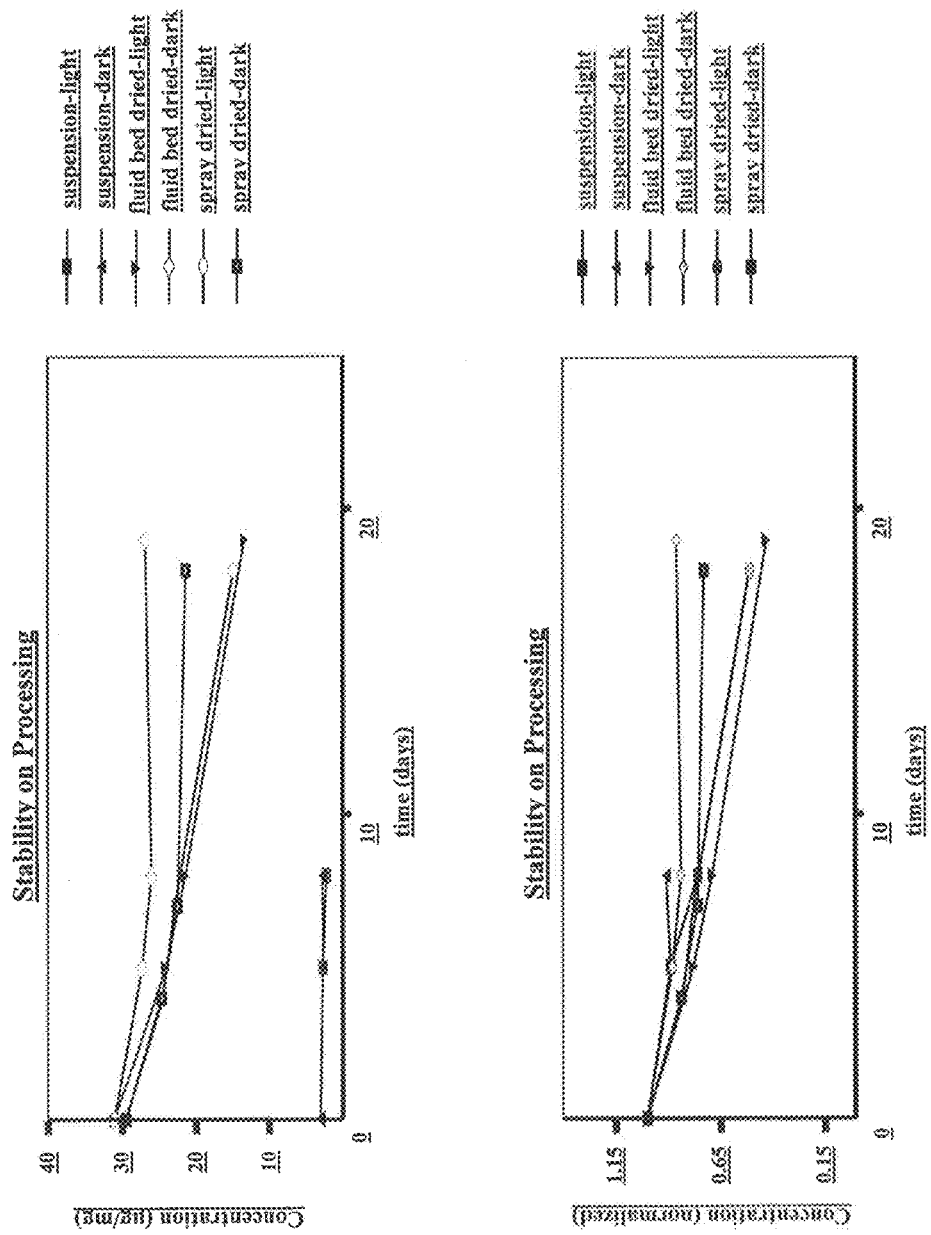
FIG. 16 is two graphs depicting the stability of various beta-carotene geode formulations over a 20 day period.
Figure 17:
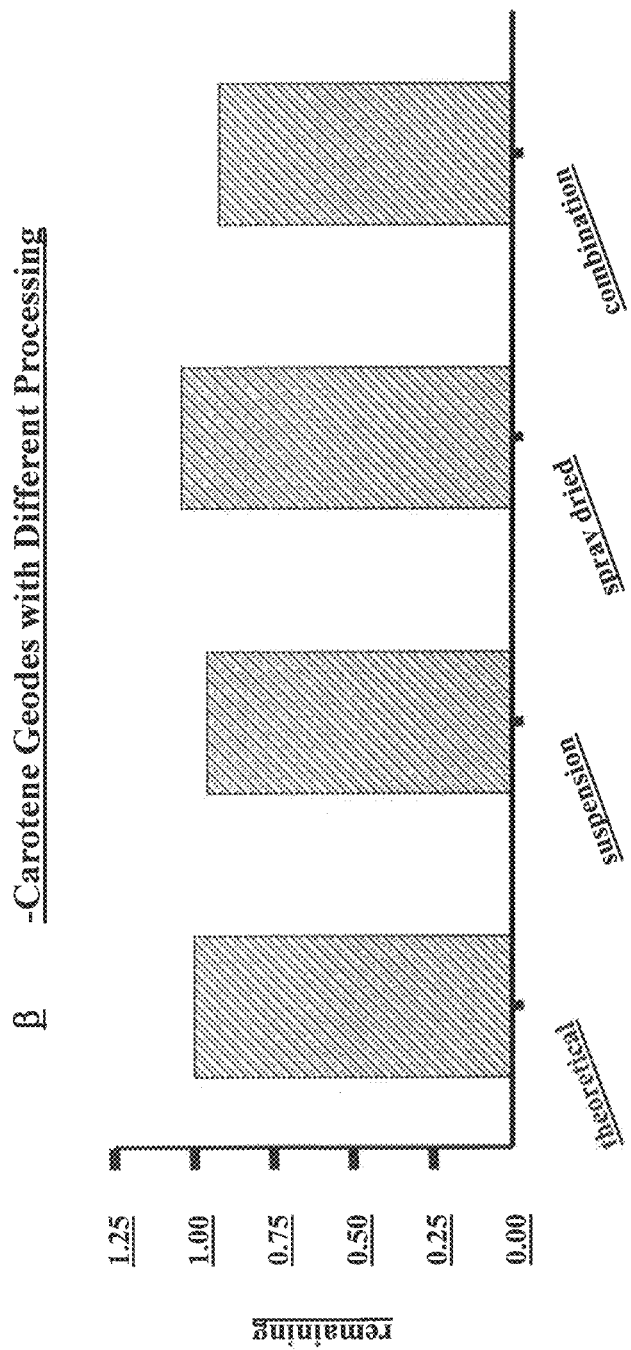
FIG. 17 is a graph showing the stability of beta-carotene geodes in suspension and after spray drying.

In order to determine whether the geodes could be successfully dried to a powder (removed from suspension) using commercial large-scale equipment and without compromising the active agent disposed therein, one batch was dried using fluid bed drying equipment by Glatt Air Techniques, Inc. (Ramsey, N.J.), and the other using spray drying equipment by Spray-Tech (Ontario, Calif.). FIGS. 15, 16 and 17 are graphs depicting the stability of beta-carotene geodes after fluid bed drying and spray drying. FIG. 15 shows the amount of beta-carotene in the formulation of geodes in suspension, after fluid bed drying, and after spray drying compared to a theoretical 100%. FIG. 17 shows similar data for beta-carotene geodes in suspension, after spray drying, and, a combination of two batched of spray-dried geodes. Concentrations of beta carotene after drying are slightly higher than expected based on the amount present in starting material, possibly due to some loss of other components. Higher recoveries of beta carotene were observed in the oil droplets within the geodes as compared to beta carotene elsewhere. FIG. 16 is a graph showing the concentration of various formulations of geodes stored for a 20 day period in the presence and absence of light. The bottom graph has been normalized to a starting concentration of 1, so that a comparison of formulations can be made. The decrease in concentration in powder upon storage may be exaggerated due to the hygroscopic geode powder taking on water.

In the fluid bed process, the geodes experienced temperatures of at least 85° C., and in the spray dried process, the geodes experienced temperatures of up to 375° F. to 400° F., in some instances (where the geodes stuck to the processing equipment) for several hours. The beta-carotene in the geodes remained active for both batches, as indicated by the red-yellow color of the samples, including the geodes removed from the processing equipment.

Figure 14A:
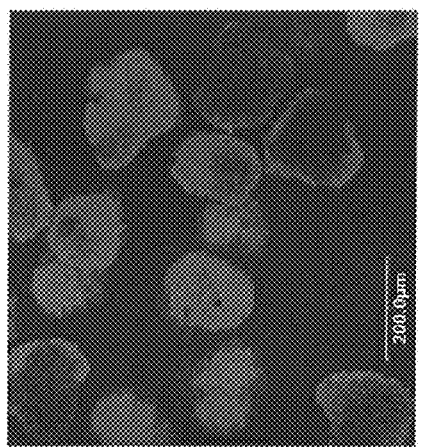
FIGS. 14A-D are images of beta-carotene geodes extracted from suspension in commercial drying apparatus.
Figure 14B:
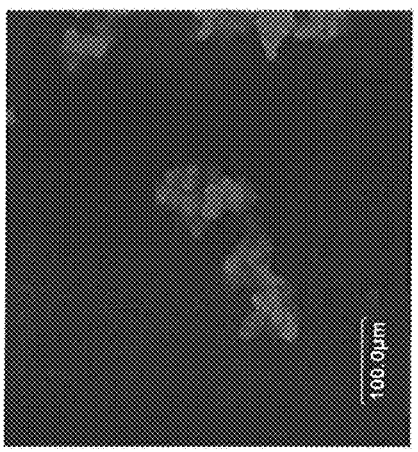
Figure 14C:
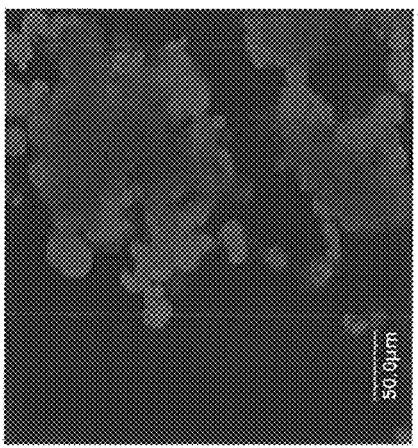
Figure 14D:
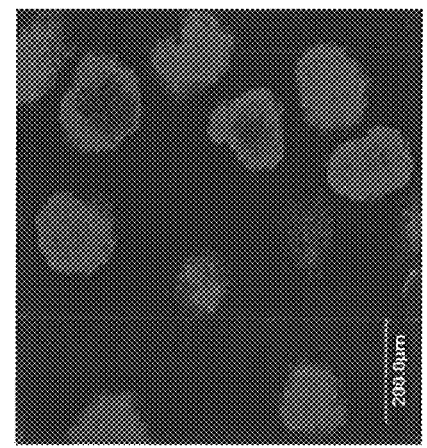

Images of the geodes indicated that the geodes were successfully prepared and that the beta-carotene was still active (FIGS. 14A-D). FIGS. 14A and 14D are images of geodes extracted by spray drying, and FIGS. 14B and 14C are images of geodes extracted by fluid bed drying.

Samples of the geodes were subsequently exposed to light and air for 2½ days, and no degradation of beta-carotene was observed.

Final Composition:

| Component | Weight | % before Ca$^+$ | % after Ca$^+$ |
|---|---|---|---|
| PS | 156 g | 60% | 49.2% |
| casein | 62.4 g | 24% | 19.7% |
| tocopherol | 2.6 g | 1% | 0.8% |
| B-carotene | 39 g (with olive oil) | 3% | 2.5% |
| olive oil | | 12% | 9.8% |
| CaCl | 57.33 g | | 18.1% |
| sterile water | 2080 ml | | |

Example 13

Preparation of NSAID Geodes

NSAID (ibuprofen and/or naproxen) was thoroughly mixed in olive oil (5% to 10% by weight of total geode mixture). Soy PS in a lipid to drug ratio of 10:1 was added to a test tube. The NSAID/olive oil mixture was then added to the tube containing powdered soy PS, and a spatula was used to thoroughly mix the powder with the oil.

Once a homogeneous paste formed, TES buffer (pH 7.4) was slowly added to the tube and vortexed for 10 to 15 minutes to further mix the suspension. The sample was observed under an optical microscope to ensure NSAID crystals were not free in suspension, but contained in the oil. Calcium chloride at 2:1 ratio to lipid was added to the stable emulsion. Sample was again observed under dark optical microscopy to determine that geodes had formed and there were no free NSAID crystals in the aqueous environment. The crystals were then stored under nitrogen at 4° C. until further use.

Prophetic Example

Assay for Nitrite Concentration

Accumulated nitrite (NO$_2^-$) in culture medium will be measured using an automated colorimetric assay based on the Griess reaction. Swierkosz, T. A., et al. Br. J. Pharmacol.; 114(7): 1335-42, 1995. Gross, S., et al. Biochem. Biophys. Res. Commun 178, 823-829, 1991. Ryu, Y. S., et al. Biochem. Biophys. Res. Comm 272, 758-764, 2000. J774A.1 mouse macrophages will be incubated with LPS (1 µg/ml) plus IFN-γ (10 µg/ml) in the presence or absence of free ibuprofen, ibuprofen cochleates, ibuprofen geodes as prepared in Example 13, free naproxen, naproxen cochleates, naproxen geodes as prepared in Example 13, and empty cochleates for 15 hours. 100 µl of sample will be reacted with the Griess reagent at room temperature for 10 minutes. $NO_2^-$ will then be determined by measuring the absorbance at 540 nm in a microplate reader. A standard curve will be obtained using known concentrations of sodium nitrite. In all experiments, $NO_2^-$ concentration in wells containing medium only will also be measured as a blank control.

EQUIVALENTS

Those skilled in the art will recognize, or be able to ascertain using no more than routine experimentation, many equivalents to the specific embodiments of the invention described wherein. Such equivalents are intended to be encompassed by the following claims.

What is claimed is:

1. A geodate cochleate, comprising:
   a lipid monolayer comprising an anionic phospholipid surrounding an oil droplet, wherein the anionic phospholipid has an anionic head group and a hydrophobic tail;
   a lipid strata comprising alternating divalent cations and anionic phospholipid bilayers, wherein the lipid strata surrounds the lipid monolayer;
   a hydrophobic or amphiphilic cargo moiety within the oil droplet, and
   wherein divalent cations form a bridge between the anionic head groups of the lipid monolayer surrounding the oil droplet and the anionic head groups of the anionic phospholipid bilayers to form the lipid strata.

2. The geodate cochleate of claim 1, wherein the geodate cochleate is suspended in an aqueous environment.

3. The geodate cochleate of claim 1, wherein the geodate cochleate further comprises a hydrophilic cargo moiety within the lipid strata.

4. The geodate cochleate of claim 1, wherein the geodate cochleate is in powder form.

5. The geodate cochleate of claim 1, wherein the lipid strata comprises at least about 50% negatively charged lipid.

6. The geodate cochleate of claim 1, wherein the lipid strata comprises at least about 75% negatively charged lipid.

7. The geodate cochleate of claim 3, wherein the hydrophobic or amphiphilic cargo moiety or the hydrophilic cargo moiety is at least one member selected from the group consisting of a nutrient, a toxin, a microbicide, a microbistat, a co-factor, an enzyme, a lipid, a pigment, a flavor agent, a hormone, a virus, an organelle a metabolic poison, an antigen, an imaging agent, a sweetener and a drug.

8. The geodate cochleate of claim 7, wherein the drug is at least one member selected from the group consisting of a protein, a small peptide, a bioactive polynucleotide, an anesthetic, an anti-infectious, an anticancer, an immunosuppressant, a steroidal anti-inflammatory, a non-steroidal anti-inflammatory, an antioxidant, an antidepressant which can be synthetic or naturally derived, an anticonvulsant, a non-nucleophilic reverse transcriptase inhibitor, a cytokine, a tranquilizer or a vasodilatory agent.

9. The geodate cochleate of claim 7, wherein the drug is at least one member selected from the group consisting of Amphotericin B, acyclovir, adriamycin, carbamazepine, ivermectin, melphalen, nifedipine, indomethacin, curcumin, ibuprofen, naproxen, steroids, phenyloin, ergotamines, cannabinoids, rapamycin, propanadid, propofol, alphadione, echinomycin, miconazole nitrate, teniposide, hexamethylmelamine, taxol, taxotere, piroxicam, diazepam, verapamil, vancomycin, tobramycin, geldanamycin, acetaminophen, aspirin, nystatin, rifampin, vitamin A acid, mesalamine, risedronate, nitrofurantoin, dantrolene, etidronate, caspofungin, nicotine, amitriptyline, clomipramine, citalopram, dothepin, doxepin, fluoxetine, imipramine, lofepramine, mirtazapine, nortriptyline, paroxetine, reboxitine, sertraline, trazodone, venlafaxine, dopamine, St. John's wort amastatin, antipain, bestatin, benzamidine, chymostatin, 3,4-dichloroisocoumarin, elastatinal, leupeptin, pepstatin, 1,10-phenanthroline, phosphoramidon, ethosuximide, ethotoin, felbamate, fosphenyloin, lamotrigine, levitiracetam, mephenyloin, methsuximide, oxcarbazepine, phenobarbital, phensuximide, primidone, topirimate, trimethadione, zonisamide, saquinavir, ritonavir, indinavir, nelfinavir, or amprenavir.

10. The geodate cochleate of claim 8, wherein the bioactive polynucleotide is at least one member selected from the group consisting of a deoxyribonucleic acid (DNA) molecule, a ribonucleic acid (RNA) molecule, an siRNA, a ribozyme, an antisense molecule, a polynucleotide modified to have a morpholino backbone, and a plasmid.

11. The geodate cochleate of claim 8, wherein the protein is at least one member selected from the group consisting of cyclosporin, angiotensin I, angiotensin II, angiotensin III, enkephalins and their analogs, ACTH, anti-inflammatory peptides I, anti-inflammatory peptides II, anti-inflammatory peptides III, bradykinin, calcitonin, beta-endorphin, dinorphin, leucokinin, leutinizing hormone releasing hormone (LHRH), insulin, neurokinins, somatostatin, substance P, thyroid releasing hormone (TRH), and vasopressin.

12. The geodate cochleate of claim 7, wherein the antigen is at least one member selected from the group consisting of a carbohydrate, envelope glycoproteins from viruses, an animal cell membrane protein, a plant cell membrane protein, a bacterial membrane protein and a parasitic membrane protein.

13. The geodate cochleate of claim 7, wherein the nutrient is at least one member selected from the group consisting of vitamins, minerals, a lipid, amino acids, fish oils, fish oil extracts, resveratrol, biotin, choline, inositol, ginko, a phytochemical and saccharides.

14. The geodate cochleate of claim 13, wherein the nutrient is the phytochemical.

15. The geodate cochleate of claim 7, wherein the nutrient is at least one member selected from the group consisting of beta-carotene, lutein, zeaxanthine, quercetin, silibinin, perillyl alcohol, genistein, sulfurophane, lycopene, omega-3 and omega-6 fatty acids.

16. The geodate cochleate of claim 13, wherein the vitamin is at least-one member selected from the group consisting of vitamins A, B, B1, B2, B3, B12, B6, B-complex, C, D, E, and K.

17. The geodate cochleate of claim 13, wherein the mineral is at least one member selected from the group consisting of boron, chromium, colloidal minerals, colloidal silver, copper, manganese, potassium, selenium, vanadium, vanadyl sulfate, calcium, magnesium, barium, iron and zinc.

18. The geodate cochleate of claim 13, wherein the lipid is a fatty acid.

19. The geodate cochleate of claim 7, wherein the sweetener is at least one member selected from the group consisting of saccharine, isomalt, maltodextrine, aspartame, glucose, maltose, dextrose, fructose and sucrose.

20. The geodate cochleate of claim 7, wherein the flavor agent is at least one oil or extract selected from the group consisting of oils and extracts of cinnamon, vanilla, almond, peppermint, spearmint, chamomile, geranium, ginger, grapefruit, hyssop, jasmine, lavender, lemon, lemongrass, marjoram, lime, nutmeg, orange, rosemary, sage, rose, thyme, anise, basil, black pepper, tea or tea extracts, an herb and a citrus.

21. The geodate cochleate of claim 1, wherein the geodate cochleate further comprises an aggregation inhibitor.

22. The geodate cochleate of claim 21, wherein the aggregation inhibitor comprises methylcellulose.

23. A pharmaceutical composition comprising a geodate cochleate of claim 1 and a pharmaceutically acceptable carrier.

24. The geodate cochleate of claim 7, wherein the pigment comprises a tetrapyrrolic pigment.

25. The geodate cochleate of claim 7, wherein the nutrient is at least one nutrient selected from the group consisting of a micronutrient and an amino acid.

26. The geodate cochleate of claim 8, wherein the drug is at least one drug selected from the group consisting of an antibiotic and an antifungal.

27. The geodate cochleate of claim 9, wherein the steroid is at least one steroid selected from the group consisting of estrogens, testosterones, 18-hydroxydeoxycorticosterone, prednisolone, dexamethazone, cortisone and hydrocortisone.

28. The geodate cochleate of claim 7, wherein the pigment is a carotenoid.

29. The geodate cochleate of claim 1, wherein the cargo moiety is Amphotericin B.

30. The geodate cochleate of claim 7, wherein the drug is an antiviral.

31. The geodate cochleate of claim 7, wherein the drug is an HIV protease inhibitor.

32. The geodate cochleate of claim 1, wherein the divalent cation is selected from the group consisting of $Ca^{2+}$, $Mg^{2+}$, $Zn^{2+}$ and $Ba^{2+}$.

33. The geodate cochleate of claim 1, wherein the divalent cation is $Ca^{2+}$.

34. The geodate cochleate of claim 3, wherein the hydrophobic or amphiphilic cargo moiety or the hydrophilic cargo moiety is at least one member selected from the group consisting of a nutrient, a toxin, a microbicide, a microbistat, a co-factor, an enzyme, a lipid, a pigment, a flavor substance, a hormone, a virus, an organelle a metabolic poison, an antigen, an imaging agent, a sweetener and a drug.

35. The pharmaceutical composition of claim 23, wherein the pharmaceutical composition is suitable for oral delivery.

36. The geodate cochleate of claim 1, wherein the geodate cochleate is in a food product.

37. The geodate cochleate of claim 36, wherein the food product is a food product consumed by humans.

38. A geodate cochleate, comprising:
a lipid monolayer comprising an anionic phospholipid surrounding an oil droplet, wherein the anionic phospholipid has an anionic head group and a hydrophobic tail;
a lipid strata comprising alternating divalent cations and anionic phospholipid bilayers, wherein the lipid strata surrounds the lipid monolayer; and
a hydrophobic or amphiphilic cargo moiety within the oil droplet,
wherein divalent cations form a bridge between the anionic head groups of the lipid monolayer surrounding the oil droplet and the anionic head groups of the anionic phospholipid bilayers to form the lipid strata,
wherein the geodate cochleate is prepared by a method comprising:
(a) mixing the anionic phospholipid with an oil to form an emulsion comprising liposomes and the lipid monolayer comprising the anionic phospholipid surrounding the oil droplet;
(b) adding the hydrophobic or amphiphilic cargo moiety;
(c) adding a divalent cation to the emulsion to form the lipid strata surrounding the lipid monolayer.

39. The geode cochleate of claim 38, wherein the hydrophobic or amphiphilic cargo moiety is added before the emulsion is formed.

40. A geodate cochleate, comprising:
a lipid monolayer comprising an anionic phospholipid surrounding a hydrophobic domain;
alternating layers of divalent cations and anionic phospholipid bilayers, wherein the alternating layers of divalent cations and anionic phospholipid bilayers surround the lipid monolayer; and
a hydrophobic or amphiphilic cargo moiety within the hydrophobic domain.

41. The geode cochleate of claim 40, wherein the alternating layers of divalent cations and anionic phospholipid bilayers are formed by introducing a divalent cation into an emulsion containing liposomes composed of anionic phospholipid bilayers.

* * * * *